US006808714B2

United States Patent
Dame et al.

(10) Patent No.: US 6,808,714 B2
(45) Date of Patent: Oct. 26, 2004

(54) DETECTION OF *SARCOCYSTIS NEURONA*

(75) Inventors: John B. Dame, Gainesville, FL (US); Siobhan P. Ellison, Fairfield, FL (US); Charles A. Yowell, Gainesville, FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 09/962,993

(22) Filed: Sep. 24, 2001

(65) Prior Publication Data

US 2002/0115828 A1 Aug. 22, 2002

Related U.S. Application Data

(60) Provisional application No. 60/234,676, filed on Sep. 22, 2000.

(51) Int. Cl.[7] .................... A61K 39/002; A61K 31/70; C12P 21/04; C07H 21/04
(52) U.S. Cl. ................ 424/269.1; 424/265.1; 424/192.1; 424/191.1; 424/185.1; 424/184.1; 424/178.1; 424/134.1; 435/69.7; 435/70.1; 435/70.21; 435/71.1; 536/23.4; 514/44
(58) Field of Search ................ 424/134.1, 178.1, 424/184.1, 185.1, 191.1, 192.1, 265.1, 269.1; 435/69.7, 70.1, 70.21, 71.1; 514/44; 536/23.4; 436/518, 523, 528, 543

(56) References Cited

U.S. PATENT DOCUMENTS

| 5,747,476 A | 5/1998 | Russell et al. |
| 5,830,893 A | 11/1998 | Russell |
| 5,883,095 A | 3/1999 | Granstrom et al. |
| 5,935,591 A | 8/1999 | Rossignol et al. |
| 6,110,665 A | 8/2000 | Fenger et al. |
| 6,344,337 B1 | 2/2002 | Mansfield et al. |

FOREIGN PATENT DOCUMENTS

| WO | WO 00/17640 | 3/2000 |
| WO | WO 00/49049 | 8/2000 |

OTHER PUBLICATIONS

Rudinger et al, in "Peptide Hormones", edited by Parsons, J.A., University Park Press, Jun. 1976, p. 6.*
Burgess et al., The Journal of Cell Biology, 111:2129–2138, 1990.*
Lazar et al., Molecular and Cellular Biology, 8(3): 1247–1252, 1988.*
Jobling et al. (Mol. Microbiol, 1991, 5(7): 1755–67.*
Liang et al 1998 (Infection and Immunity; 66 (5) 1834–1838).*

* cited by examiner

*Primary Examiner*—Lynette R. F. Smith
*Assistant Examiner*—Padma Baskar
(74) *Attorney, Agent, or Firm*—Saliwanchik, Lloyd & Saliwanchik

(57) ABSTRACT

A gene encoding a 29 kilodalton protein found on the surface of merozoite stage *S. neurona* has been cloned and sequenced. The protein encoded by this gene, termed SnSAG-1, is an immunodominant antigen recognized on protein blots. Methods for using nucleic acids and polypeptides relating to SnSAG-1 in diagnostic tests and vaccine development are disclosed.

11 Claims, No Drawings

DETECTION OF *SARCOCYSTIS NEURONA*

CROSS REFERENCE TO RELATED APPLICATION

The present application claims the priority of U.S. provisional patent application No. 60/234,676 filed Sep. 22, 2000.

STATEMENT AS TO FEDERALLY SPONSORED RESEARCH

This invention was made with United States Government support under grant number 98-35204-6487 awarded by the United States Department of Agriculture. The U.S. government may have certain rights in the invention.

FIELD OF THE INVENTION

The invention relates generally to the fields of microbiology and veterinary medicine. More particularly, the invention concerns compositions and methods relating to detecting *Sarcocystis neurona*.

BACKGROUND

Equine Protozoal Myeloencephalitis (EPM) is a common cause of neurologic disease in New World horses. It is caused by a parasite termed *Sarcocystis neurona* (*S. neurona*), an obligatory intracellular apicomplexan parasite whose multi-phase life cycle is completed in either one or two hosts. *S. neurona* is known to cycle naturally between opossums and both none-banded armadillos and striped skunks. Horses typically become infected by consuming infectious parasite stages found in opossum feces. Once a horse has been infected, *S. neurona* can travel to the brain and spinal cord, where merozoite stages of this parasite replicate and cause pathology.

Horses with EPM typically present with lameness, but may alternatively or additionally present with symptoms characteristic of primary brain disease. Because the parasite can inhabit any area of the central nervous system (CNS) of the horse, symptoms associated with EPM can vary widely. The degree of infection can range from subtle to severe and can involve the brain and/or the spinal cord. EPM is usually progressive.

Presently, a definitive diagnosis of EPM is made by post-mortem examination, where *S. neurona* organisms are identified in histological lesions. The organ may also be cultured from the lesion. The presence of the organism in the histologic section or when cultured from the lesion establishes the diagnosis. Heretofore, pre-mortem methods for diagnosing EPM were based on assays using whole merozoites, and not a purified protein, to probe for the presence of anti-*S. neurona* antibodies (as an indication of infection) in the horses. The use of such whole merozoites results in significant cross-reaction with non-*S. neurona* specific antibodies (e.g., those against other Sarcocystis species). This cross-reactivity obscures interpretation of results using whole merozoite-based assays.

SUMMARY

The invention relates to the discovery and characterization of a 29 kilodalton (kDa) protein found on the surface of merozoite stage *S. neurona*. This antigen, termed SnSAG-1 or SnSMA1, is an immunodominant antigen recognized on protein blots. Using purified or recombinant SnSAG-1 (i.e., rSnSAG-1) antigen, accurate assays for diagnosing EPM in horse pre-mortem have been developed. These assays involve identifying a marker indicative of the presence of the 29 kDa antigen or an antibody to this antigen in a sample to be tested. Thus, because a single purified antigen or marker is utilized in such assays, the cross-reactivity problems associated with whole-merozite based assays are obviated or much reduced.

A cDNA copy of the mRNA which encodes the SnSAG-1 antigen has been cloned from a gene library prepared from an isolate of *S. neurona*. The original clone was identified in a collection of random sequence tags prepared to characterize the cDNA library. Additional clones of the same gene sequence were obtained to identify a full length gene. The nucleotide sequence of a full-length gene clone was determined. This sequence or the clone itself can be used to gusto prepare the SnSAG-1 antigen in a recombinant or other synthetic form for use in diagnostic tests and vaccine development.

Accordingly, the invention features a composition for detecting the presence of *S. neurona* in a biological sample. In one variation, the composition includes a SnSAG-1 marker that is a purified nucleic acid including a nucleotide sequence that encodes a protein that shares at least 50% or at least 90% sequence identity with SEQ ID NO:1. In this variation, the nucleotide sequence can also encode the protein of SEQ ID NO:1. For example, the nucleotide sequence can be SEQ ID NO:3.

In a second variation of the composition, the SnSAG-1 marker is a purified polynucleotide that binds under stringent hybridization conditions to a complement of the nucleotide sequence SEQ ID NO:3, wherein the polynucleotide is at least 30 (e.g., 50, 100, or 200) nucleotides in length.

In a third variation of the composition, the SnSAG-1 marker is an isolated protein including a polypeptide that shares at least 50%, 70%, 90%, or 95% sequence identity with a fragment of the amino acid sequence of SEQ ID NO:1 that is at least 20, 50, 100, or 300 contiguous residues in length. For example, the polypeptide can include at least 20, 50, 100, or 300 contiguous amino acid residues of the sequence of SEQ ID NO:1. The polypeptide can also include the entire amino acid sequence of SEQ ID NO:1. In this composition, the protein can be a fusion protein or a recombinant protein.

In a fourth variation of the composition, the SnSAG-1 marker is a purified antibody that specifically binds to a polypeptide consisting of the amino acid sequence of SEQ ID NO:1, wherein the antibody is a monoclonal antibody or a monospecific polyconal antibody. The purified antibody can be labeled with a detectable label such as a radioisotope, a fluorescent compound, a bioluminescent compound, a chemiluminescent compound, biotin, colloidal gold, a magnetic particle, or an enzyme.

In another aspect, the invention features a method for detecting *Sarcocystis neurona* in a biological sample. This method includes the steps of: (a) providing the biological sample; and (b) analyzing the biological sample for the presence of a SnSAG-1 marker that is a nucleic acid including a nucleotide sequence that encodes a protein that shares at least 50% sequence identity with SEQ ID NO:1; a polynucleotide that binds under stringent hybridization conditions to a complement of the nucleotide sequence SEQ ID NO:3, wherein the polynucleotide can be at least 30 nucleotides in length; a protein including a polypeptide that shares at least 50% sequence identity with a fragment of the amino acid sequence of SEQ ID NO:1 that can be at least 20 contiguous residues in length; or an antibody that specifically binds to a polypeptide consisting of the amino acid sequence of SEQ ID NO:1. In this method, the presence of the SnSAG-1 marker in the biological sample indicates that the biological sample contains *Sarcocystis neurona*.

In the variation of this method where the SnSAG-1 marker is a nucleic acid including a nucleotide sequence that encodes a protein that shares at least 50% sequence identity with SEQ ID NO:1, the nucleotide sequence can be SEQ ID NO:3.

In the variation of this method where the SnSAG-1 marker is a protein including a polypeptide that shares at least 50% sequence identity with a fragment of the amino acid sequence of SEQ ID NO:1 at least 20 contiguous residues in length, the polypeptide can include at least 20 contiguous amino acid residues of the sequence of SEQ ID NO:1. For example, the polypeptide can include the amino acid sequence of SEQ ID NO:1.

The biological sample of the method can include CNS tissue, CSF, blood, or serum. It can also be derived from a horse.

In this method of the inevtnion, the step (B) of analyzing the biological sample for the presence of a SnSAG-1 marker can include isolating RNA from the sample, generating cDNAs from the isolated RNA, and amplifying the cDNAs by PCR to generate a PCR product. The step (B) of analyzing the biological sample for the presence of a SnSAG-1 marker can also include contacting the sample with a labeled oligonucleotide probe that hybridizes under stringent hybridization conditions to the nucleotide sequence SEQ ID NO:3 or a complement of the nucleotide sequence SEQ ID NO:3; or contacting the sample to a molecule that specifically binds to an antibody that specifically binds a protein consisting of the amino acid sequence of SEQ ID NO:1. In the latter, the molecule can be immobilized on a substrate.

In one variation of the method, the biological sample includes SnSAG-1 specific antibodies that are specifically bound to the molecule immobilized on substrate. The antibodies can be detected using a secondary antibody that is labeled with a detectable label. For example, the secondary antibody can specifically bind horse immunoglobulin. The detectable label can be a radioisotope, a fluorescent compound, a bioluminescent compound, a chemiluminescent compound, biotin, colloidal gold, a magnetic particle, or an enzyme (e.g., peroxidase or alkaline phosphatase).

In another variation of this method, the step (B) of analyzing the biological sample for the presence of a SnSAG-1 marker includes contacting the sample with a molecule that specifically binds a protein consisting of the amino acid sequence of SEQ ID NO:1. The molecule can be an antibody such as a monoclonal antibody or a monospecific polyclonal antibody. In this variation, the antibody can be labeled with a detectable label.

The invention also features a composition for stimulating an immune response against *Sarcocystis neurona* when administered to an animal. The composition includes (a) an isolated agent that can specifically stimulate an immune response against a protein consisting of the amino acid sequence of SEQ ID NO:1 when administered to an animal; and (b) a pharmaceutically acceptable carrier. The composition can include an adjuvant such as an aluminum salt; an oil-in-water emulsion; a composition including saponin; a composition including a bacterial protein; or a cytokine.

The agent that can stimulate an immune response against *Sarcocystis neurona* when administered to an animal can include a nucleic acid that can be a first polynucleotide including a nucleotide sequence that encodes a protein that shares at least 50% sequence identity with SEQ ID NO:1; or a second polynucleotide that binds under stringent hybridization conditions to a complement of the nucleotide sequence SEQ ID NO:3, wherein the second polynucleotide can be at least 30 nucleotides in length. In the foregoing, the nucleic acid can be a naked DNA, a nucleic acid incorporated into an expression vector, or a polypeptide Unless otherwise defined, all technical terms used herein have the same meaning as commonly understood by one of ordinary skill in the art to which this invention belongs. Commonly understood definitions of molecular biology terms can be found in Rieger et al., Glossary of Genetics: Classical and Molecular, 5th edition, Springer-Verlag: New York, 1991; and Lewin, Genes V, Oxford University Press: New York, 1994.

By the term "gene" is meant a nucleic acid molecule that codes for a particular protein, or in certain cases, a functional or structural RNA molecule. For example, the SnSAG-1 gene encodes the SnSAG-1 protein.

As used herein, a "nucleic acid" or a "nucleic acid molecule" means a chain of two or more nucleotides such as RNA (ribonucleic acid) and DNA (deoxyribonucleic acid). A "purified" nucleic acid molecule is one that is substantially separated from other nucleic acid sequences in a cell or organism in which the nucleic acid naturally occurs (e.g., 30, 40, 50, 60, 70, 80, 90, 95, 96, 97, 98, 99, 100% free of contaminants). The term includes, e.g., a recombinant nucleic acid molecule incorporated into a vector, a plasmid, a virus, or a genome of a prokaryote or eukaryote. Examples of purified nucleic acids include cDNAs, fragments of genomic nucleic acids, nucleic acids produced polymerase chain reaction (PCR), nucleic acids formed by restriction enzyme treatment of genomic nucleic acids, recombinant nucleic acids, and chemically synthesized nucleic acid molecules. A "recombinant" nucleic acid molecule is one made by an artificial combination of two otherwise separated segments of sequence, e.g., by chemical synthesis or by the manipulation of isolated segments of nucleic acids by genetic engineering techniques.

By the terms "SnSAG-1 gene," "SnSAG-1 polynucleotide," or "SnSAG-1 nucleic acid" is meant a native SnSAG-1-encoding nucleic acid sequence, e.g., the native SnSAG-1 nucleic acid (SEQ ID NO:3); a nucleic acid having sequences from which a SnSAG-1 cDNA can be transcribed; and/or allelic variants and homologs of the foregoing. The terms encompass double-stranded DNA, single-stranded DNA, and RNA.

As used herein, the terms "protein" and "polypeptide" are used synonymously to mean any peptide-linked chain of amino acids, regardless of length or post-translational modification, e.g., glycosylation or phosphorylation. An "purified" polypeptide is one that has been substantially separated or isolated away from other polypeptides in a cell, organism, or mixture in which the polypeptide occurs (e.g., 30, 40, 50, 60, 70, 80, 90, 95, 96, 97, 98, 99, 100% free of contaminants). An "isolated" polypeptide is a purified polypeptide that is not included on a substrate (e.g., a polyacrylamide gel) with other purified polypeptides from the cell or organism in which the polypeptide occurs.

By the terms "SnSAG-1 protein" or "SnSAG-1 polypeptide" are meant an expression product of a SnSAG-1 nucleic acid (e.g., one consisting of SEQ ID NO:3), or a protein that shares at least 50% (but preferably 55, 60, 65, 70, 75, 80, 85, 90, 95, 96, 97, 98, or 99%) amino acid sequence identity with SEQ ID NO:3.

As used herein, "sequence identity" means the percentage of identical subunits at corresponding positions in two sequences when the two sequences are aligned to maximize subunit matching, i.e., taking into account gaps and insertions. When a subunit position in both of the two sequences is occupied by the same monomeric subunit, e.g., if a given position is occupied by an alanine in each of two polypeptide molecules, then the molecules are identical at that position. For example, if 7 positions in a sequence 10 amino acids in length are identical to the corresponding positions in a second 10 amino acid sequence, then the two sequences have 70% sequence identity. Likewise, if 7 positions in a sequence 10 nucleotides in length are identical to the corresponding positions in a second 10-nucleotide sequence, then the two sequences have 70% sequence identity. Preferably, the length of the compared sequences is at least 60 nucleotides, more preferably at least 75 nucleotides, and most preferably 100 nucleotides. Sequence identity can be measured using sequence analysis software (e.g., one or more of the algorithms of MegAlign™ sequence analysis software from DNA STAR, Inc., Madison, Wis.).

When referring to hybridization of one nucleic to another, "low stringency conditions" means in 10% formamide, 5×Denhart's solution, 6×SSPE, 0.2% SDS at 42° C., followed by washing in 1×SSPE, 0.2% SDS, at 50° C.; "moderate stringency conditions" means in 50% formamide, 5×Denhart's solution, 5×SSPE, 0.2% SDS at 42° C., followed by washing in 0.2× SSPE, 0.2% SDS, at 65° C.; and "high stringency conditions" means in 50% formamide, 5× Denhart's solution, 5×SSPE, 0.2% SDS at 42° C., followed by washing in 0.1×SSPE, and 0.1% SDS at 65° C. The phrase "stringent hybridization conditions" means low, moderate, or high stringency conditions.

A "fragment" of a SnSAG-1 nucleic acid is a portion of a SnSAG-1 nucleic acid that is less than full-length and comprises at least a minimum length capable of hybridizing specifically with a native SnSAG-1 nucleic acid under stringent hybridization conditions. The length of such a fragment is preferably at least 15 nucleotides, more preferably at least 20 nucleotides, and most preferably at least 30 nucleotides of a native SnSAG-1 nucleic acid sequence. A "fragment" of a SnSAG-1 polypeptide is a portion of a SnSAG-1 polypeptide that is less than full-length (e.g., a polypeptide consisting of 5, 10, 15, 20, 30, 40, 50, 75, 100 or more amino acids of a native SnSAG-1 protein).

When referring to a nucleic acid molecule or polypeptide, the term "native" refers to a naturally-occurring (e.g., a "wild-type") nucleic acid or polypeptide. A "homolog" of a SnSAG-1 gene is a gene sequence encoding a SnSAG-1 polypeptide isolated from an organism other than a human being. Similarly, a "homolog" of a native SnSAG-1 polypeptide is an expression product of a SnSAG-1 gene homolog.

As used herein, a "SnSAG-1 marker" is any molecule whose presence in a sample (e.g., a cell) indicates that a SnSAG-1 gene or protein is present in the sample or subject from which the sample was derived. SnSAG-1 markers include SnSAG-1 nucleic acids, SnSAG-1 proteins, and antibodies that specifically bind SnSAG-1 proteins. "Expressing a SnSAG-1 gene" or like phrases mean that a sample contains a transcription product (e.g., messenger RNA, i.e., "mRNA") of a SnSAG-1 gene or a translation product of a SnSAG-1 protein-encoding nucleic acid (e.g., a SnSAG-1 protein). A cell expresses a SnSAG-1 gene when it contains a detectable level of a SnSAG-1 nucleic acid or a SnSAG-1 protein.

By the term "antibody" is meant an immunoglobulin as well as any portion or fragment of an immunoglobulin whether made by enzymatic digestion of intact immunoglobulin or by techniques in molecular biology. The term also refers to a mixture containing an immunoglobulin (or portion or fragment thereof) such as an antiserum.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), the specified ligand or antibody binds to its particular "target" (e.g. anti-SnSAG-1 antibody specifically binds to an SnSAG-1polypeptide) and does not bind in a significant amount to other proteins present in the sample or to other proteins to which the ligand or antibody may come in contact in an organism.

By the phrase "stimulating an immune response" is meant eliciting or increasing the activation of a lymphocyte (e.g., a B cell or T cell) or other immune system component. The stimulation of an immune response against a specific antigen can be measured as an increase in antibody titer against that antigen or the activation of one or more lymphocytes having a surface receptor specific for the antigen. Activation of lymphocytes can be determined by conventional assays, e.g., the induction of mitosis, secretion of cytokines, modulation of cell surface molecule expression, secretion of immunoglobulin (B cells), and increased killing of target cells (cytotoxic T cells).

Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. In addition, the particular embodiments discussed below are illustrative only and not intended to be limiting.

DETAILED DESCRIPTION

A gene encoding a *S. neurona* surface antigen has been cloned and sequenced. The antigen encoded by the gene has been characterized. Rabbit anti-*S. neurona* polyclonal antibody was used to immunoprecipitate and concentrate proteins of an isolate of *S. neurona* for detection of antibodies in body fluids of clinically ill horses. The serum and cerebral spinal fluid (CSF) of diseased animals was used to identify antigens important in natural infections. Techniques were developed to separate parasites from host cells facilitating production a cDNA expression library. The library was screened with both polyclonal rabbit anti-*S. neurona* and mass culture supernatant from hybridoma cells produced from mice immunized with the *S. neurona* isolate. A cone was also identified in a collection of random sequence tags prepared to characterize the cDNA library.

A gene fragment was cloned from the library and used as a probe to select the full length copy of the gene encoding a major surface antigen, SnSAG-1, of *S. neurona.* The sequence data from the full length gene was used to generate PCR primers for producing an amplicon containing the open reading frame of SnSAG-1 with flanking BamH1 restriction sites. This approach allowed the gene to be sub-cloned into the BamH1 site of the expression vector pET14b which allows expression of a His-tagged recombinant protein (i.e., His-tagged rSnSAG-1). This recombinant protein migrated slightly larger on SDS-PAGE than the native antigen.

A monoclonal antibody that specifically binds an epitope of the 29 kDa protein (corresponding to SnSAG-1) from cultured *S. neurona* merozoites was used to verify the presence of the epitope on the recombinant protein. The recombinant protein was purified and used to produce a monospecific polyclonal antibody in mice and goats. The anti-SnSAG-1 antisera was used to characterize the 29 kDa antigen of cultured *S. neurona* merozoites as a surface protein.

The cloned DNA sequence was used as a probe to determine the relative abundance and size of the gene transcript on an RNA blot. Additionally, probing Southern blots indicated that the gene was present in genomic DNA of *S. neurona* but not other species (*S. falcatula, T. gondii*, or *Neospora hughesii*).

This invention encompasses compositions and methods relating to SnSAG-1. The below described preferred embodiments illustrate adaptations of these compositions and methods. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning: A Laboratory Manual, 2nd ed., vol. 1–3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Various techniques using polymerase chain reaction (PCR) are described, e.g., in Innis et al., PCR Protocols: A Guide to Methods and Applications, Academic Press: San Diego, 1990: PCR-primer pairs can be derived from known sequences by known techniques such as using computer programs intended for that purpose (e.g., Primer, Version 0.5, ©©1991, Whitehead Institute for Biomedical Research, Cambridge, Mass.). The Reverse Transcriptase Polymerase Chain Reaction (RT-PCR) method used to identify and amplify certain polynucleotide sequences within the invention was performed as described in Elek et al., In Vivo, 14:172–182, 2000). Methods for chemical synthesis of nucleic acids are discussed, for example, in Beaucage and Carruthers, Tetra. Letts. 22:1859–1862, 1981, and Matteucci et al., J. Am. Chem. Soc. 103:3185, 1981. Chemical synthesis of nucleic acids can be performed, for example, on commercial automated oligonucleotide synthesizers. Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992.

Nucleic Acids

The present invention includes the SnSAG-1 gene of *S. neurona*. The nucleotide sequence of the gene encoding SnSAG-1 along with some adjacent sequences is shown herein as SEQ ID NO:2. The region of this nucleic acid encoding the native SnSAG-1 protein (see SEQ ID NO:3) is found in positions 73–903 (SEQ ID NO:3).

A preferred nucleic acid molecule of the invention is the native SnSAG-1 polynucleotide shown herein as SEQ ID NO:3. Another nucleic acid of the invention includes a purified nucleic acid (polynucleotide) that encodes a polypeptide having the amino acid sequence of SEQ ID NO:1. As the native SnSAG-1 gene was cloned from a gene library of the UCD-1 isolate of *S. neurona*, nucleic acid molecules encoding a polypeptide of the present invention can be obtained from such a library or from the isolate itself by conventional cloning methods such as those described herein.

Nucleic acid molecules of the present invention may be in the form of RNA or in the form of DNA (e.g., cDNA, genomic DNA, and synthetic DNA). The DNA may be double-stranded or single-stranded, and if single-stranded may be the coding (sense) strand or non-coding (anti-sense) strand. The coding sequence which encodes the native SnSAG-1 protein may be identical to the nucleotide sequence shown herein as SEQ ID NO:3. It may also be a different coding sequence which, as a result of the redundancy or degeneracy of the genetic code, encodes the same polypeptide as the polynucleotide of SEQ ID NO:3. Other nucleic acid molecules within the invention are variants of the native SnSAG-1 gene such as those that encode fragments, analogs and derivatives of a native SnSAG-1 protein. Such variants may be, e.g., a naturally occurring allelic variant of the native SnSAG-1 gene, a homolog of the native SnSAG-1 gene, or a non-naturally occurring variant of the native SnSAG-1 gene. These variants have a nucleotide sequence that differs from the native SnSAG-1 gene in one or more bases. For example, the nucleotide sequence of such variants can feature a deletion, addition, or substitution of one or more nucleotides of the native SnSAG-1 gene. Nucleic acid insertions are preferably of about 1 to 10 contiguous nucleotides, and deletions are preferably of about 1 to 30 contiguous nucleotides.

Variant SnSAG-1 proteins displaying substantial changes in structure can be generated by making nucleotide substitutions that cause less than conservative changes in the encoded polypeptide. Examples of such nucleotide substitutions are those that cause changes in (a) the structure of the polypeptide backbone; (b) the charge or hydrophobicity of the polypeptide; or (c) the bulk of an amino acid side chain. Nucleotide substitutions generally expected to produce the greatest changes in protein properties are those that cause non-conservative changes in codons. Examples of codon changes that are likely to cause major changes in protein structure are those that cause substitution of (a) a hydrophilic residue, e.g., serine or threonine, for (or by) a hydrophobic residue, e.g., leucine, isoleucine, phenylalanine, valine or alanine; (b) a cysteine or proline for (or by) any other residue; (c) a residue having an electropositive side chain, e.g., lysine, arginine, or histadine, for (or by) an electronegative residue, e.g., glutamine or aspartine; or (d) a residue having a bulky side chain, e.g., phenylalanine, for (or by) one not having a side chain, e.g., glycine.

Naturally occurring allelic variants of the native SnSAG-1 gene within the invention are nucleic acids isolated from *S. neurona* that have at least 75% (e.g., 76%, 77%, 78%, 79%, 80%, 81%, 82%, 83%, 84%, 85%, 86%, 87%, 88%, 89%, 90%, 91%, 92%, 93%, 97%, 98%, and 99%) sequence identity with the native SnSAG-1 gene, and encode polypeptides having structural similarity to native SnSAG-1 protein. Homologs of the native SnSAG-1 gene within the invention are nucleic acids isolated from other species that have at least 50% (e.g., 50%, 51%, 52%, 53%, 54%, 55%, 56%, 57%, 58%, 59%, 60%, 61%, 62%, 66%, 67%, 68%, 69%, 70%, 71%, 72%, 73%, 74%, 75%, 76%, 77%, 78%, 82%, 83%, 84%, 85%, 86%, 87%, 88%, 89%, 90%, 91%, 92%, 93%, 94%, 98%, and 99%) sequence identity with the native SnSAG-1 gene, and encode polypeptides having structural similarity to native SnSAG-1 protein. Public and/or proprietary nucleic acid databases can be searched to identify other nucleic acid molecules having a high percent (e.g., 70, 80, 90% or more) sequence identity to the native SnSAG-1 gene.

Non-naturally occurring SnSAG-1 gene variants are nucleic acids that do not occur in nature (e.g., are made by the hand of man), have at least 50% (e.g., 50%, 51%, 52%, 53%, 54%, 55%, 56%, 57%, 58%, 59%, 60%, 61%, 62%, 63%, 64%, 65%, 66%, 67%, 71%, 72%, 73%, 74%, 75%, 76%, 77%, 78%, 79%, 80%, 81%, 82%, 83%, 87%, 88%, 89%, 90%, 91%, 92%, 93%, 94%, 95%, 96%, 97%, 98%, and 99%) sequence identity with the native SnSAG-1 gene, and encode polypeptides having structural similarity to native SnSAG-1 protein (e.g., those that cross react with antibodies that specifically bind the native SnMS1 protein). Examples of non-naturally occurring SnSAG-1 gene variants are those that encode a fragment of a SnSAG-1 protein, those that hybridize to the native SnSAG-1 gene or a complement of to the native SnSAG-1 gene under stringent hybridization conditions, those that share at least 50% sequence identity with the native SnSAG-1 gene or a complement of the native SnSAG-1 gene, and those that encode an SnSAG-1 fusion protein.

Nucleic acids encoding fragments of native SnSAG-1 protein within the invention are those that encode, e.g., 2, 5, 10, 25, 50, 100, 150, 200, 250, or more amino acid residues of the native SnSAG-1 protein. Shorter oligonucleotides (e.g., those of 6, 7, 8, 9, 10, 11, 12, 13, 14, 15, 16, 17, 18, 19, 20, 30, 50, 100, 125, 150 or 200 base pairs in length) that encode or hybridize with nucleic acids that encode fragments of the native SnSAG-1 protein can be used as probes, primers, or antisense molecules. Longer polynucleotides (e.g., those of 300, 400, 500, 600, 700, or 800 base pairs) that encode or hybridize with nucleic acids that encode fragments of native SnSAG-1 protein can also be used in various aspects of the invention. Nucleic acids encoding fragments of native SnSAG-1 protein can be made by enzymatic digestion (e.g., using a restriction enzyme) or chemical degradation of the full length native SnSAG-1 gene or variants thereof.

Nucleic acids that hybridize under stringent hybridization conditions to the nucleic acid of SEQ ID NO:3 or the complement of SEQ ID NO:3 can also be used in the invention. For example, such nucleic acids can be those that hybridize to SEQ ID NO:3 or the complement of SEQ ID NO:3 under low stringency conditions, moderate stringency conditions, or high stringency conditions are within the invention. Preferred such nucleotide acids are those having a nucleotide sequence that is the complement of all or a portion of SEQ ID NO:3. Other variants of the native SnSAG-1 gene within the invention are polynucleotides that share at least 50% (e.g.,50, 55, 60, 65, 70, 75, 80, 85, 90, 91, 92, 93, 94, 95, 96, 97, 98, and 99%) sequence identity to SEQ ID NO:3 or the complement of SEQ ID NO:3. Nucleic acids that hybridize under stringent hybridization conditions to or share at least 50% sequence identity with SEQ ID NO:3 or the complement of SEQ ID NO:3 can be obtained by techniques known in the art such as by making mutations in the native SnSAG-1 gene, or by isolation from an organism expressing such a nucleic acid (e.g., an allelic variant).

Nucleic acid molecules encoding SnSAG-1 fusion proteins are also within the invention. Such nucleic acids can be made by preparing a construct (e.g., an expression vector) that expresses an SnSAG-1 fusion protein when introduced into a suitable host. For example, such a construct can be made by ligating a first polynucleotide encoding an SnSAG-1 protein fused in frame with a second polynucleotide encoding another protein (or a HIS tag) such that expression of the construct in a suitable expression system yields a fusion protein.

The oligonucleotides of the invention can be modified at the base moiety, sugar moiety, or phosphate backbone, for example, to improve stability of the molecule, hybridization, etc. Oligonucleotides within the invention may additionally include other appended groups such as peptides (e.g., for targeting host cell receptors in vivo), or agents facilitating transport across the cell membrane (see, e.g., Letsinger et al. (1989) Proc. Natl. Acad. Sci. U.S.A. 86:6553–6556; Lemaitre et al. (1987) Proc. Natl. Acad. Sci. USA 84:648–652; PCT Publication No. WO 88/09810, published Dec. 15, 1988), hybridization-triggered cleavage agents. (See, e.g., Krol et al. (1988) BioTechniques 6:958–976) or intercalating agents. (See, e.g., Zon (1988) Pharm. Res. 5:539–549). To this end, the oligonucleotides may be conjugated to another molecule, e.g., a peptide, hybridization triggered cross-linking agent, transport agent, hybridization-triggered cleavage agent, etc.

Using the nucleotide of the native SnSAG-1 gene and the amino acid sequence of the native SnSAG-1 protein previously reported, those skilled in the art can create nucleic acid molecules that have minor variations in their nucleotide, by, for example, standard nucleic acid mutagenesis techniques or by chemical synthesis. Variant SnSAG-1 nucleic acid molecules can be expressed to produce variant SnSAG-1 proteins.

Polypeptides

The gene sequence shown herein as SEQ ID NO:3 encodes the native SnSAG-1 protein shown herein as SEQ ID NO:1. The native SnSAG-1 protein is predicted to have a molecular weight of 28,328 daltons and an isoelectric point (pI) of 7.48. It is a Type Ia membrane protein with a putative signal peptide, one transmembrane spanning region at its C terminus, and is presently believed to be anchored in the merozoite membrane via a glycophosphatidyl inositol (GPI) linkage. It has a potential cleavage site at residue 248.

The present invention provides a purified SnSAG-1 polypeptide encoded by a nucleic acid of the invention such as that shown as SEQ ID NO:3. A preferred form of SnSAG-1 polypeptide is a purified native SnSAG-1 protein that has the deduced amino acid sequence shown herein as SEQ ID NO:1. Polypeptide variants of native SnSAG-1 protein such as fragments, analogs and derivatives of the native SnSAG-1 protein are also within the invention. Such variants include, e.g., a polypeptide encoded by a naturally occurring allelic variant of native SnSAG-1 gene, a polypeptide encoded by an alternative splice form of the native SnSAG-1 gene, a polypeptide encoded by a homolog of native SnSAG-1 gene, and a polypeptide encoded by a non-naturally occurring variant of native SnSAG-1 gene.

SnSAG-1 polypeptide variants have a peptide sequence that differs from native SnSAG-1 in one or more amino acids. The peptide sequence of such variants can feature a deletion, addition, or substitution of one or more amino acids of a native SnSAG-1 protein. Amino acid insertions are preferably of about 1 to 4 contiguous amino acids, and deletions are preferably of about 1 to 10 contiguous amino acids.

SnSAG-1 protein fragments corresponding to one or more particular motifs and/or domains or to arbitrary sizes, for example, at least 5, 10, 25, 50, 75, 100, 125, 150, 175, 200, and 250 amino acids in length are within the scope of the present invention. Isolated peptidyl portions of SnSAG-1 polypeptides can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. Particularly preferred SnSAG-1 protein fragments are those that are specifically bound by antibodies developed against the whole native SnMSA protein and those antibodies that specifically bind whole *S. neurona* merozoites with little or no detectable cross-reaction to other species.

Another aspect of the present invention concerns recombinant forms of the SnSAG-1 polypeptides. Exemplary recombinant polypeptides of the present invention, in addition to native SnSAG-1 protein, are encoded by a nucleic acid that has at least 85% sequence identity (e.g., 85, 86, 87, 88, 89, 90, 91, 92, 93, 94, 95, 96, 97, 98, 99, 100%) with the nucleic acid sequence of SEQ ID NO:3.

The invention also provides for reduction of SnSAG-1 polypeptides to generate mimetics, e.g., peptide or non-peptide agents, that are able to disrupt binding of a SnSAG-1 protein to other proteins or molecules with which the native SnSAG-1 protein interacts. For instance, non-hydrolyzable peptide analogs of such residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J. Med. Chem. 29:295; and Ewenson et al. in Peptides: Structure and Function (Proceedings of the 9th American Peptide Symposium) Pierce Chemical Co. Rockland, Ill., 1985), beta-turn dipeptide cores (Nagai et al. (1985) Tetrahedron Lett 26:647; and Sato et al. (1986) J. Chem. Soc. Perkin. Trans. 1:1231), and b-aminoalcohols (Gordon et al. (1985) Biochem. Biophys. Res. Commun. 126:419; and Dann et al. (1986) Biochem. Biophys. Res. Commun. 134:71). SnSAG-1 polypeptides may also be chemically modified to create SnSAG-1 derivatives by forming covalent or aggregate conjugates with other chemical moieties, such as glycosyl groups, lipids, phosphate, acetyl groups and the like. Covalent derivatives of SnSAG-1 can be prepared by linking the chemical moieties to functional groups on amino acid side chains of the protein or at the N-terminus or at the C-terminus of the polypeptide.

The present invention further pertains to methods of producing the subject SnSAG-1 polypeptides. For example, a host cell (e.g., *E. coli*) transfected with a nucleic acid vector directing expression of a nucleotide sequence encoding the subject polypeptides can be cultured under appropriate conditions to allow expression of the peptide to occur. The cells may be harvested, lysed, and the protein isolated. A recombinant SnSAG-1 polypeptide can be isolated from host cells using techniques known in the art for purifying proteins including ion-exchange chromatography, gel filtration chromatography, ultrafiltration, electrophoresis, and immunoaffinity purification with antibodies specific for such protein.

After SnSAG-1 protein has been expressed in a cell, it can be isolated using any immunoaffinity chromatography. For instance, an anti-SnSAG-1 antibody (e.g., produced as described below) can be immobilized on a column chromatography matrix, and the matrix can be used for immuno-affinity chromatography to purify SnSAG-1 protein from cell lysates by standard methods (see, e.g., Ausubel et al., supra). After immuno-affinity chromatography, SnSAG-1 protein can be further purified by other standard techniques, e.g., high performance liquid chromatography (see, e.g., Fisher, Laboratory Techniques In Biochemistry And Molecular Biology, Work and Burdon, eds., Elsevier, 1980). In another embodiment, SnSAG-1 protein is expressed as a fusion protein containing an affinity tag (e.g., GST) that facilitates its purification.

Antibodies

SnSAG-1 polypeptides (or immunogenic fragments or analogs thereof) can be used to raise antibodies useful in the invention. Such polypeptides can be produced by recombinant techniques or synthesized as described above. In general, SnSAG-1 polypeptides can be coupled to a carrier protein, such as KLH, as described in Ausubel et al., supra, mixed with an adjuvant, and injected into a host mammal. Antibodies produced in that animal can then be purified by peptide antigen affinity chromatography. In particular, various host animals can be immunized by injection with a SnSAG-1 polypeptide or an antigenic fragment thereof. Commonly employed host animals include rabbits, mice, guinea pigs, and rats. Horses are preferred for the production of equine antibodies and for many of the methods described herein. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Other potentially useful adjuvants include BCG (bacille Calmette-Guerin) and *Corynebacterium parvum*.

Polyclonal antibodies are heterogeneous populations of antibody molecules that are contained in the sera of the immunized animals. Antibodies within the invention therefore include polyclonal antibodies and, in addition, monoclonal antibodies, single chain antibodies, Fab fragments, F(ab')$_2$ fragments, and molecules produced using a Fab expression library. Monoclonal antibodies, which are homogeneous populations of antibodies to a particular antigen, can be prepared using the SnSAG-1 polypeptides described above and standard hybridoma technology (see, for example, Kohler et al., Nature 256:495, 1975; Kohler et al., Eur. J. Immunol. 6:511, 1976; Kohler et al., Eur. J. Immunol. 6:292, 1976; Hammerling et al., "Monoclonal Antibodies and T Cell Hybridomas," Elsevier, N.Y., 1981; Ausubel et al., supra). In particular, monoclonal antibodies can be obtained by any technique that provides for the production of antibody molecules by continuous cell lines in culture such as described in Kohler et al., Nature 256:495, 1975, and U.S. Pat. No. 4,376,110; the human B-cell hybridoma technique (Kosbor et al., Immunology Today 4:72, 1983; Cole et al., Proc. Natl. Acad. Sci. USA 80:2026, 1983), and the EBV-hybridoma technique (Cole et al., "Monoclonal Antibodies and Cancer Therapy," Alan R. Liss, Inc., pp. 77–96, 1983). Such antibodies can be of any immunoglobulin class including IgG, IgM, IgE, IgA, IgD and any subclass thereof. A hybridoma producing a mAb of the invention may be cultivated in vitro or in vivo. The ability to produce high titers of mAbs in vivo makes this a particularly useful method of production.

Techniques described for the production of single chain antibodies (e.g., U.S. Pat. Nos. 4,946,778, 4,946,778, and 4,704,692) can be adapted to produce single chain antibodies against an SnSAG-1 polypeptide, or a fragment thereof. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include but are not limited to F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed (Huse et al., Science 246:1275, 1989) to allow rapid and easy identification of monoclonal Fab fragments with the desired specificity.

Preferably, SnSAG-1 polypeptide selective antibodies of the invention are produced using fragments of SnSAG-1 that lie outside highly conserved regions and appear likely to be antigenic, by criteria such as high frequency of charged residues. Cross-reactive anti-SnSAG-1 antibodies are produced using a fragment of SnSAG-1 that is conserved amongst members of this family of proteins. In one specific example, such fragments are generated by standard techniques of PCR, and are then cloned into the pGEX expression vector (Ausubel et al., supra). Fusion proteins are expressed in *E. coli* and purified using a glutathione agarose affinity matrix as described in Ausubel, et al., supra.

Once produced, polyclonal or monoclonal antibodies or fragments thereof can be tested for specific SnSAG-1 recognition by Western blot or immunoprecipitation analysis by standard methods, for example, as described in Ausubel et al., supra. Antibodies that specifically recognize and bind to SnSAG-1 polypeptide are useful in the invention.

The antibodies of the invention can be used, for example, in the detection of an SnSAG-1 polypeptide in a biological sample (e.g., serum or CSF from a horse). Antibodies also can be used in a screening assay to measure the effect of a candidate compound on expression or localization of SnSAG-1 polypeptides. Additionally, such antibodies can be used to interfere with the interaction of SnSAG-1 polypeptides and other molecules that bind SnSAG-1 polypeptides.

Methods of Detecting *S. neurona*

This invention is also related to the use of a SnSAG-1 nucleic acid as part of a diagnostic assay for detecting the presence of *S. neurona* in a biological sample (e.g., an *S. neurona* infection is a horse). For example, nucleic acid is isolated from a biological sample such as from the CSF, blood, urine, saliva, tissue biopsy or necropsy material taken from an animal. The isolated nucleic acid may be used directly for detection or may be amplified enzymatically by using PCR (Saiki et al., Nature, 324: 163–166 (1986)) prior to analysis. RNA or cDNA may also be used for the same purpose. As an example, oligonucleotides complementary to the nucleic acid encoding an SnSAG-1 polypeptide can be used as probes or PCR primers to identify and analyze the isolated nucleic acid for the presence of nucleotide sequences encoding the SnSAG-1 polypeptide.

As one example, nucleic acid from a biological sample (e.g., nerve tissue or CSF from a horse) is isolated from the sample (e.g., by PCR amplification) and then immobilized on a substrate (e.g., by UV cross-linking to a blotting membrane). The substrate is then contacted with a labeled (e.g., chemiluminescent or radioactive) nucleic acid probe that hybridizes to an SnSAG-1 nucleic acid under stringent hybridization conditions. After washing the substrate to remove unbound probe, the amount of labeled probe bound to the substrate is assessed (e.g., by exposing the substrate to photographic or X-ray film). Binding of probe to the immobilized nucleic acid indicates the presence of a nucleic acid encoding an SnSAG-1 polypeptide in the biological sample. Specific nucleic acid sequences may also be detected using methods such as other types of hybridization, RNase protection, chemical cleavage, direct DNA sequencing or the use of restriction enzymes, (e.g., Restriction Fragment Length Polymorphism analysis (RFLP)), Northern blotting of mRNA, and Southern blotting of genomic DNA). Assays used to detect the presence or amount of SnSAG-1 polypeptide in a biological sample are also within the invention. Examples of such assays include radioimmunoassay, competitive-binding assays, Western Blot analysis, ELISA assays and "sandwich" assays. As one example, a typical ELISA assay can be performed by first preparing an antibody that specifically binds to an SnSAG-1 polypeptide. The antibody, which can be monoclonal or polyclonal, is then conjugated to a detectable label such as an enzyme (e.g., horseradish peroxidase). A biological sample to be tested (e.g., CSF from a horse) is then immobilized on a solid substrate, e.g., by incubating the sample on a polystyrene dish that has been treated to bind proteins contained in the sample. Free protein binding sites on the substrate are then blocked by adding a non-specific protein like albumin on the substrate. After washing the substrate, the anti-SnSAG-1 antibody is contacted to the substrate under conditions that allow the antibody to bind any SnSAG-1 polypeptide attached to the substrate. The substrate is then washed to remove any unbound antibody. Antibody remaining attached to the substrate is then detected to provide a quantitative estimate of the amount of SnSAG-1 polypeptide in the biological sample. Attached antibody can be detected via the detectable label. For example, horseradish peroxidase labeled antibodies can be detected by adding an appropriate substrate that produces a color change in the presence of horseradish peroxidase. As another example, a competition assay may be employed wherein antibodies that specifically bind a SnSAG-1 polypeptide are attached to a solid support and labeled-SnSAG-1 protein and a sample derived from a biological sample are passed over the solid support. The amount of label not binding to the solid support can be detected, for example by liquid scintillation chromatography, and correlated to a quantity of SnSAG-1 polypeptide in the sample (more label not bound to the support correlates with more SnSAG-1 polypeptide in the sample).

Methods of Detecting *S. neurona*-specific Antibodies

Methods of detecting the presence of antibodies that specifically bind to a SnSAG-1 polypeptide are also within the invention. As one exemplary method, an SnSAG-1 polypeptide (e.g., rSnMSA protein or fragment thereof) is immobilized on a substrate (e.g., immobilized on a blotting membrane or in the wells of microtiter plate). After washing, a biological sample (e.g., blood or serum from a horse) is added to the substrate under conditions that allow any anti-SnSAG-1 antibodies present in the sample to bind to the immobilized SnSAG-1 polypeptide. After again washing the substrate to remove any unbound antibody, a reagent that detects bound antibody is added to the substrate and allowed to bind any antibody attached to the substrate. The reagent can, for example, take the form of a labeled-secondary antibody that binds to anti-SnSAG-1 antibody (e.g., for horse blood, the antibody could be a horseradish peroxidase-conjugated anti-horse immunoglobulin antibody). Unbound reagent is then washed away, and the amount of attached reagent is assessed as an indication of the presence of anti-SnSAG-1 antibodies in the sample (more reagent correlates with more antibody). Variations of the foregoing and other methods of detecting anti-SnSAG-1 antibodies within the invention include radioimmunoassay, competitive-binding assays, Western Blot analysis, ELISA assays and "sandwich" assays.

Kits for Detecting S. neurona

The invention also provides a kit for detecting S. neurona either directly or indirectly (e.g., by detecting antibodies produced against S. neurona by an animal's immune system). The kit can feature one or more of the nucleic acids, polypeptides, or antibodies of the invention; various devices and reagents for performing one of the assays described herein (e.g., blotting membranes, microtiter plates, labeled-secondary antibodies, etc.); and/or printed instructions for using the kit to detect S. neurona or an antigen or nucleic acid thereof.

Vaccines-method of Inducing an Immune Response

The invention also includes a composition for use in a vaccine against S. neurona. In one embodiment, the composition includes an SnSAG-1 polypeptide (e.g., native SnSAG-1 protein) and an adjuvant such as Freund's adjuvant (complete and incomplete), aluminum hydroxide, a surface active substance (e.g., lysolecithin, pluronic polyols, polyanions, peptides, oil emulsions, keyhole limpet hemocyanin, and dinitrophenol). Such a composition can be injected into an animal to induce an immune response (e.g., production of antibodies against the SnSAG-1 polypeptide or a cytotoxic T cell response). Nucleic acids within the invention (e.g., that of SEQ ID NO:3) can also be used as a vaccine by adapting known techniques. See, e.g., Wolff et al., Science 247, 1465–1468, 1990.

Vaccines within the invention include an antigenic agent which can take the form of any substance that can evoke or increase an immune response against SnSAG-1 when introduced into a subject. Typical immune responses include (a) the production of, or increase in titer of, antibodies that specifically bind SnSAG-1 and (b) the activation of T lymphocytes (e.g., to kill a target cell or provide help in the activation of antibody production in B lymphocytes). A number of different antigenic agents have been shown to be effective in stimulating an immune response against a protein antigen, including, for example, protein-and peptide-based vaccines, tumor-cell vaccines, dendritic cell/gene therapy vaccines and DNA/viral vaccines. See, e.g., Greten, T. F. and E. M. Jaffee, J. Clin. Oncol., 17: 1047–1060, 1999. In addition to the foregoing, various substances such as adjuvants and excipients/carriers can be included in the vaccine compositions of the invention to non-specifically enhance the antigen-specific immune response stimulated by the antigenic agent and to facilitate delivery of the other components of the vaccine to a subject.

Protein/Peptide Based Vaccines

The antigenic agent for use in the vaccines of the invention can take the form of the native SnSAG-1 protein (SEQ ID NO:1) or a peptide fragment thereof. Vaccines made with the whole protein antigen are advantageous because they have the capability of stimulating an immune response against all of the potential antigenic sites expressed by the protein. Vaccines made with peptide antigens (e.g., 7–15 or 8–12 contiguous amino acids of the whole protein), on the other hand, will generally stimulate an immune response against fewer than all of the potential antigenic sites expressed by the protein. Peptide-based vaccines are sometimes advantageous over whole protein-based vaccines where it is desired to more specifically target the stimulated immune response, e.g., to avoid undesired cross reactions. For example, peptides for use in the vaccine can be selected to correspond to (1) specific epitopes of the antigens that are known to be presented by MHC class I or MHC class II molecules, or (2) a modified form of an epitope that either exhibits an increased stability in vivo or a higher binding affinity for an MHC molecule than the native epitope, while still being capable of specific activation of T-cells. See, Ayyoub et al., J. Biol. Chem., 274: 10227–10234, 1999; Parkhurst et al., Immunol., 157: 2539–2548, 1996. Peptide-based vaccines have been shown to circumvent immune tolerance to the intact proteins. Disis et al., J. Immunol., 156: 3151–3158, 1996. In addition to vaccines composed of only one type of peptide fragment, other vaccines within the invention also include those made up of a cocktail of several different peptides derived from the native SnSAG-1 protein.

Vaccines within the invention can include a SnSAG-1 protein other than the native SnSAG-1 protein as an antigenic agent. For example, variants of the native SnSAG-1 protein such as fragments, analogs and derivatives of native SnSAG-1 are also contemplated for use as an antigenic agent in the vaccines of the invention. Such variants include, e.g., a polypeptide encoded by a naturally occurring allelic variant of the native SnSAG-1 gene, a polypeptide encoded by a homolog of the native SnSAG-1 gene, and a polypeptide encoded by a non-naturally occurring variant of the native SnSAG-1 gene. Preferred versions of such variants are those that are able to stimulate a protective immune response to native SnSAG-1 upon administration to a subject as part of a vaccine.

Nucleic Acid-based Vaccines

Nucleic acid-based vaccines are known to elicit a prominent cell-mediated immune response. See, e.g., Donnely et al., 1997; Rosenberg, S. A., Immunity 10:281, 1999. Thus, in addition to protein/peptide based vaccines, the antigenic agent for use in the vaccines of the invention can take the form of a nucleic acid that can stimulate an immune response against SnSAG-1 when administered to a subject. Examples of such nucleic acids include those that encode the native SnSAG-1 protein such as the nucleic acid shown herein as SEQ ID NO:3, a variant of the native SnSAG-1, or a peptide fragment of that native or variant SnSAG-1. Vaccines made with a nucleic acid that encodes the whole protein antigen are advantageous because they have the potential for stimulating an immune response against all of the different antigenic sites expressed by the protein. Vaccines made with a nucleic acid that encodes a peptide antigen (e.g., 7–15 amino acids of the whole protein), on the other hand, will generally stimulate an immune response against fewer than all of the potential antigenic sites expressed by the protein.

The form of the nucleic acid used in a vaccine of the invention can be any suitable for stimulating an immune response SnSAG-1 when administered to a subject. For example, the nucleic acid can be in the form of "naked DNA" or it can be incorporated in an expression vector.

Nucleic acids that are most immunogenic in a subject can be determined by preparing several of a particular SnSAG-1 nucleic acid (e.g., one that encodes the whole antigen or peptide fragments thereof), administering the subject (or a series of genetically similar such subjects) such nucleic acids in a vaccine composition (e.g., as naked nucleic acid or in an expression vector in a suitable carrier), and analyzing the subject(s) for the stimulation of an immune response. Those nucleic acids that induce the desired response can then be selected.

Naked Nucleic Acid Vaccines

The invention provides for the use of naked nucleic acid vaccines to stimulate an immune response against SnSAG-1. Representative naked nucleic acid vaccines for use in this method include a DNA encoding one or more immunogenic portions of SnSAG-1 along with sufficient other 5' and 3' elements to direct expression of the foregoing. The use of naked nucleic acids for stimulating both class I and class II restricted immune responses against a particular protein is known in the art. See, e.g., Rosenberg, S. A., Immunity 10:281, 1999; Ulmer et al., Science, 259:1745, 1993; Donnelly et al., Ann. NY Acad. Sci., 772:40, 1995; Scheurs et al., Cancer res. 58:2509, 1998; Hurpin et al., Vaccine 16:208, 1998; Lekutis et al., J. Immunol. 158:4471, 1997; Manickan et al., J. Leukoc. Biol. 61:125, 1997. These methods can be adapted for use in the present invention by using a nucleic acid encoding one or more immunogenic portions of SnSAG-1. Naked nucleic acid vaccines can be administered to a subject by any suitable technique. For example, naked DNA encoding a peptide portion of SnSAG-1 can be injected into muscle cells of a subject or naked DNA-coated gold particles can be introduced into skin cells (to be taken up by dendritic cells) of a subject using a gene gun.

Expression Vector Vaccines

The invention also provides for the use of expression vector vaccines to stimulate an immune response against SnSAG-1. In a typical application of this technique, a nucleic acid encoding one or more peptide or protein antigens of SnSAG-1 is incorporated into a vector that allows expression of the antigen(s) in a host cell (e.g., a cell inside a subject or administered to a subject). The nucleic acid encoding the antigen(s) is generally be under the operational control of other sequences contained within the vector such as a promoter sequences (e.g., tissue specific, constitutively active, or inducible) or enhancer sequences. The antigen(s) encoded by the vector are expressed when the vector is introduced into a host cell in a subject. After expression, the antigen(s) can associate with an MHC molecule for presentation to immune system cells such as T lymphocytes, thus stimulating an immune response. See, e.g., Corr et al., J. Exp. Med. 184:1555 (1996). Vectors for use in the invention can be any capable of expressing an encoded antigen(s) in a subject. For example, vectors derived from bacterial plasmids and viruses may be used. Representative viral vectors include retroviral, adenoviral, and adeno-associated viral vectors.

Administering Vaccines to a Subject

The vaccine compositions of the present invention can be used in a method for stimulating an immune response against SnSAG-1 in a subject (e.g., a horse). In this method, an vaccine compositon of the invention can be administered to a subject by any method that stimulates the aforesaid immune response. The exact method selected is determined by the particular vaccine composition to administered. For parenteral administration by injection, the injection can be in situ (i.e., to a particular tissue or location on a tissue, e.g., into a tumor or lymph node), intramuscular, intravenous, intraperitoneal, or by another parenteral route. For example, for a protein/peptide based vaccine the vaccine may be administered by subcutaneous or intradermal injection. In some cases other routes can be used, e.g. intravenous injection, intraperitoneal injection, or in situ injection into target tissue.

Naked nucleic acid vaccines or expression vector vaccines may be administered by intramuscular injection. Cell-based vaccines can be introduced into an animal by any suitable method, e.g., subcutaneous injection. In addition to parenteral routes, the vaccines of the invention can also be administered by a non-parenteral route, e.g, by oral, buccal, urethral, vaginal, or rectal administration.

Formulations for injection may be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the vaccine compositions may be in powder form (e.g., lyophilized) for constitution with a suitable vehicle, for example, sterile pyrogen-free water, before use.

To facilitate delivery of the antigenic compositions (e.g., antigenic agent plus adjuvant) of the invention to an animal, the antigenic compositions can be mixed with a pharmaceutically acceptable carrier or excipient. Examples of such pharmaceutically acceptable carriers and excipients include diluents such as water, saline, citrate buffered saline, phosphate buffered saline, acetate buffered saline, and bicarbonate buffered saline; and stabilizing agents such as amino acids, alcohols, proteins (for example, serum albumin), EDTA, mannitol, sorbitol, and glycerol. To minimize the chance of infection or adverse reaction when administered to a subject, carriers and excipients are preferably sterile and pyrogen-free. USP grade carriers and excipients are particularly preferred for delivery of vaccine compositions to human subjects. The vaccine compositions can also be formulated for long-term release as a depot preparation by adding the antigenic agent to suitable polymeric or hydrophobic materials or ion exchange resins. They can also be made by preparing the vaccine composition as a sparingly soluble derivative. Depot preparations can be administered to a subject by implantation (e.g., subcutaneous or intramuscular surgical implantation) or by injection. Methods for making the foregoing formulations are well known and can be found in, for example, *Remington's Pharmaceutical Sciences*.

Dosing

The vaccine compositions of the invention are preferably administered to a subject in an amount sufficient to stimulate an immune response against *S. neurona* in the subject, and not cause an overly toxic effect. Such a therapeutically effective amount can be determined as described below.

Toxicity and therapeutic efficacy of the vaccines utilized in the invention can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Vaccines that exhibit large therapeutic indices are preferred. While those that exhibit toxic side effects may be used, care should be taken to design a delivery system that minimizes the potential damage of such side effects. The dosage of preferred vaccines lies preferably within a range that include an $ED_{50}$ with little or no toxicity. The dosage may vary within this range depending upon the dosage form employed and the route of administration utilized.

The vaccines of the invention can be administered to a subject using various different vaccination schedules. For example, a nucleic acid vaccine might be administered to a subject only once, while a protein/peptide-based vaccine might be administered to the subject on multiple occasions (1, 2, 3, 4, 5 or more times). For example, in an effort to stimulate a strong immune response, a first dose of a vaccine compositions of the invention may be administered to a subject at least 24 hours before a second (booster) dose is administered to the subject.

Vaccine Kits

The invention also provides kits for stimulating an immune response against S. neurona in a subject. Such kits can include a container holding one or more of the antigenic agents described above in a pharmaceutically acceptable form. The antigenic agent(s) in the container can be in liquid form (e.g., as a solution) or in solid form (e.g., as a lyophilized or desiccated powder). Where, for example, the antigenic agent is a solid, the kits within the invention can further include a container holding a pharmaceutically acceptable solution (e.g., sterile saline with or without dextrose) for reconstituting the solid into a liquid suitable for injection. The kits of the invention can further include (a) one or more devices to administer the antigenic agent, e.g., a needle or syringe, a packaged alcohol pad, etc.; and/or (b) printed instructions for using the kit.

EXAMPLES

The present invention is further illustrated by the following specific examples. The examples are provided for illustration only and are not to be construed as limiting the scope or content of the invention in any way.

Example 1

Preparation of Sporocysts for In Vitro Culture

Sporocysts of S. neurona were obtained by scraping the mucosa of feral Florida opossums that had been killed on the roadways. Mucosal scrapings were stored in antibiotic media at 4° C. until used. Murphy A. J. and Mansfield, L. S., 1999 Journal of Parasitology 85(5):979–981. Sarcocystis neurona sporocyst isolates were selected from among those identified using DNA marker analysis. Dame J. B. et al. 1995 Journal of Parasitology 81(6):930–935. Prior to being placed in culture, sporocysts were treated in 5% sodium hypochlorite (bleach) for 5 min and washed in tap water by repeated cycles of centrifugation (300×g, 10 min) and resuspension until the smell of bleach was undetectable. Sporocysts were floated on an 20/30/60% isosmotic colloidal silica step gradient (Percoll®). Sporocysts obtained at the 30/60 interface were washed twice in PBS, as described above, and stored short term at 4° C. Sporozoites were excysted by either of two methods: 1) ~100 sporocysts were resuspended in 100 µl horse bile containing 2 µl trypsin (5 units/ml) and incubated for 4–6 hours at 37° C. under a 5% $CO_2$ 95% air atmosphere Sporozoites and unexcysted sporocysts were collected by centrifugation as above, washed once in phosphate buffered saline, pH 7.2 (PBS) and resuspended in a final volume of 100 µl PBS. 2) ~100 sporocysts were resuspended in PBS containing proteinase K (1 mg/ml) and 1% SDS and incubated for 10 min. at 37° C. Sporocysts were pelleted by centrifugation at 300×g for 10 min. and washed by resuspension in PBS without additives 3 times. Finally, the pellet was resuspended in 200 µl dimethyl sulfoxide (DMSO) freeze media (Fisher) and incubated for two hours to overnight at −20° C.

Half of the excysted sporocyst preparation were added to a 25 $cm^2$ flask with a freshly trypsinized, 60% confluent monolayer of BM cells in Dulbecco's medium containing 10% horse serum, 100 units/ml penicillin, 100 units/ml streptomycin, 1 mM pyruvate and 1 mM glutamate. The culture was maintained at 38° C. in an atmosphere of 5% $CO_2$, 95% air. The culture medium was changed at 24 hours and then at 2–4 day intervals. Parasite development was monitored by direct microscopic observation with a Nikon inverted microscope at 1–3 day intervals.

Example 2

Ionophore A23187—Stimulated Merozoite Release and Purification

A stock solution of calcium ionophore A23187 (Sigma) was prepared in dimethylsulfoxide to a final concentration of 1 mg/ml and stored at −20° C. Infected cell monolayers (see example 1) at 12 days post infection were washed three times with PBS or Hanks Balanced Salts Solution (HBSS), and 10 ml of A23187 (1 µM in HBSS) was added to the washed monolayer and incubated at 37° C. for 40 min. in 5% $CO_2$, 95% air. Free merozoites were collected by centrifugation and washed in PBS as above. Parasites released by this method were examined by density gradient centrifugation, but further separation from host cell debris by density gradient centrifugation was not routinely necessary. For further purification, parasites recovered from the supernatant were isolated from host cell debris on a discontinuous buoyant density gradient using Iodixanol (Optiprep) in PBS or HBSS. Merozoites were suspended gently in 1.0 ml PBS and were layered onto a preformed, three step discontinuous gradient with layers of 1.03, 1.04 and 1.06 g/ml in a 15 ml round bottom centrifuge tube. The gradient was centrifuged at 1000×g for 25 min at 20° C. with the brake off. Fractions containing particulate material at each interface were collected and examined microscopically. The fractions(s) containing significant amounts of merozoites were collected for use.

Collection of parasites free in the culture medium was enhanced 90 fold by incubation of infected host cells for 40 min in 1 µM A23187 prior to collecting the culture supernatant. Parasitized host cells that released merozoites in response to ionophore treatment were BM, BM0617, HL, BT, and ED cells. Infected GT, HFF, CHO, BHK, and primary EM cells were refractory for the release of parasites under the same conditions. The release of parasites in response to ionophore treatment was optimal at 10 to 12 days post infection, just after a few parasites were first observed free in the culture supernatant. Although difficult to accurately determine the percentage of individual merozoites released by this treatment, it was a large proportion. No mature schizonts were visible in a microscopic examination of treated cultures. Selective disruption of the parasitized-host-cell membrane was seen in electron micrographs. Initially, the host cell increased in size, became vacuolated, and had small breaks in the membrane. As the plasma membrane became more permeable, empty membrane bound vacuoles or vacuoles with peripheral ribosomes were released into the media. The host cell became long and cytoplasmic volume decreased. Parasites were observed to move beginning at 10 minutes and continuing until their release at forty minutes. The merozoites undulated hyperactively in this media, but with the removal of the ionophore by addition of culture media, released parasites and the host cells recovered a normal appearance and activity. Ionophore-treated parasites remained animated and readily infected new cells when incubated onto a fresh monolayer. The difference noted in electron micrographs of ionophore treated parasites was that they appeared to have more prominent micronemes than untreated parasites. The separation of parasites proteins after they are treated with ionophore was observed, however coomassie blue staining is not sufficient to distinguish parasite antigens from those of the host cells.

Parasites released from the host cell monolayer by A23187 were single, hyperactive, and entered cells readily. When A23187-treated parasites were used as the inoculum, the infected host cells harbored an abundance of mature schizonts in 3 to 5 days. The extracellular parasites remaining after washing off the ionophore did not re-invade ionophore-treated host cells, but increased in size while the few merozoites that remained in host cells formed mature schizonts in five days continuing the infection. Ten days after ionophore treatment, the parasites in the monolayer were unresponsive to calcium ionophore, whereas at thirty days, ionophore treatment again elicited parasite release. During this second ionophore treatment, many host cells were released into the supernatant.

Example 3

S. neurona Growth Rate and Response to Ionophore Treatment

Sarcocystis neurona was grown in 11 cell lines to determine growth rate and response to ionophore treatment of the monolayer. Sarcocystis neurona merozoites replicated in two different bovine monocyte lines [BM, laboratory stock culture and BM 0617 (American Type Culture Collection, Rockville, Md., USA) CRL 0617], bovine turbinate cells (BT cells, ATTC CRL 1390), human lung cells (HL cells, ATTC CCL 201-8Lu), human foreskin fibroblasts (HFF, ATTC CRL 2450), Chinese hamster ovary cells (CHO cells, ATTC CCL 61), bovine kidney (MDBK cells, ATTC CCL 22), goat tumor cells (GT cells, a gift of Dr. Jack Gaskin), equine dermal cells (ED cells, ATTC CRL 6288), and equine monocytes (EM, primary culture from peripheral blood). Parasite growth in each of these host cell lines was observed over a 30 day period starting from an inoculum of 2000 parasites collected from the culture supernatant of BM cells.

Typically exuberant growth with rosette formation at five days post infection when sub-cultured from BM 0617 cells. Formation of rosettes was first observed 3 days post infection with release and re-invasion of new cells occurring at five days post infection. The efficiency of infection was increased when freshly trypsinized host cells were placed in sufficient numbers in the culture flask to establish a 60% confluent monolayer immediately before merozoites were added. This increase in numbers of merozoites entering host cells improved the yield of parasites and shortened by two weeks the length of time required for culture prior to harvesting the merozoites. Infection of BT cells by merozoites was increased by 50% using scraped cells from thirty day post infection as inoculum rather that the supernatant from the same cultures.

Example 4

Examination of Parasites Found Free in Culture vs. Inside Host Cells

Studies of the replication of the parasite were performed as follows. Approximately 220 *S. neurona* merozoites recovered from a culture supernatant were added to 5000 Human Lung (HL) cells seeded and growing on Thermonax coverslips in 24 well plates to evaluate the growth and natural release of parasites. Every three days, the 2 ml supernate was removed and evaluated by cytospin and the number of merozoites present counted. The corresponding coverslip was fixed in methanol and stained with Giemsa and the total number of intracellular parasites and those extracellular, but associated with the cover slip, were counted.

Cultures of parasites replicating in HL cells were examined to follow the number of parasites free in the culture supernatant as compared with those found inside host cells during normal parasite growth. The majority of the parasites were released at 21 days in this experiment.

Lung cells at 60% confluence were seeded at a density of 0.1 merozoites per host cell and parasite growth was monitored microscopically for 30 days. Free parasites were not observed until 10 days post infection. During most of the period of observation, the percentage of extracellular parasites was less than 10%. On day 28, the largest number of free parasites was counted; but the next day the numbers of extracellular parasites was back to less than 10%. Duplicate 75 cm flasks were grown for 12 days in HL cells and treated with HBSS or HBSS with 1 $\mu$M A23187. Free parasites were collected by centrifugation and counted with a hemocytometer.

Example 5

Molecular Analysis of Parasite Cultures

DNA analysis by RAPD markers 33/54 separated the samples into those similar to *S. neurona*, but different than *S. falcatula,* and those that were falcatula-like or 1085-like as described by Tanhauser S., et al. 1999 Journal of Parasitology 85(2):221–228. Washed merozoites were pelleted by centrifugation for five minutes at 16,000 g in a microcentrifuge. The pellet was resuspended in 100 $\mu$l of lysis buffer (50 mM KCL, 10 mM Tris-HCL, pH 9.0, 1.5 mM $MgCl_2$, 1% Triton X-100, 1% Tween-20, 1 $\mu$M Proteinase K), incubated two hours at 56° C., and then boiled for two min. to inactivate the Proteinase K. The tube was centrifuged to remove particulate matter and the supernate was used directly as template in a polymerase chain reaction (PCR). A PCR amplification consisting of the following reagents assembled on ice in a thin-walled microfuge tube: 3 $\mu$l DNA template, 5 $\mu$l 10×PCR buffer, 3 $\mu$l dNTP mix (2.5 mM each), nuclease free water to 47 $\mu$l, 2 $\mu$l 33/54 RAPD screening primers. The PCR reaction was 94° C. for three min. with hot start, 35 cycles: 94° C. 30 sec, 45° C. 1 min., 72° C. 45 sec, followed by 6 min. at 72° C. The resulting PCR reaction was analyzed on a 1% agarose gel in 1×TBE with ethidium bromide (0.5 $\mu$g/ml) added to the running buffer. These RAPD markers produced a PCR product 1,100 bp. Restriction endonuclease digestions with DraI resulted in a fragment of 884 and 216 bp for *S. neurona*, and digestions with Hinf I resulted in fragments 745 and 355 for *S. falcatula.*

Example 6

2D Electrophoresis and Immunoprecipitation of *S. neurona* Antigens

*Sarcocystis neurona* was grown and washed as described in Ellison, S. P., et al. 2001 International Journal of Parasitology, followed by one wash in carbonate buffer (50 mM $Na_2CO_3$, 0.85% NaCl, pH 7.4) and centrifuged at 300×g for 10 min. Merozoites were then washed twice in Na$_2$CO$_3$ buffer at 4° C. and placed in lysis buffer (50 mM Tris-HCl, pH 7.6, 1% TritonX-100, 1 mM EDTA) at 4° C. for 30 min. Parasite lysate was centrifuged at 3000×g for 30 min. at 4° C. The pellet was resuspended in 2DE (two dimensional electrophoresis) sample buffer (8M urea, 100 mM dithiothreitol, 4% CHAPS, 0.5% carrier amphylolytes pH 3–10, and 40 mM Tris-HCl). The lysate volume was brought to 1 ml with dilution buffer to which 10 µl polyclonal rabbit anti-S. neurona serum was added and the mix was incubated 30 min. at 37° C. After incubation 150 µl washed (lysis buffer) GammaBind Plus Sepharose gel (Pharmacia) was added and incubated for 30 min. at 4° C. with shaking. The gel was washed by centrifugation in a microfuge twice with lysis buffer and once with water (to remove salt) and 135 µl 2DE sample buffer was added and held at room temperature for 30 min. followed by centrifugation at 3000 g 30 min. The supernate was removed to a new tube and centrifuged at full speed in a microfuge for 5 min. to remove any remaining gel.

A pH 3–10 IEF (Bio-Rad) strip was rehydrated overnight with 125 µl of sample followed by isoelectric focusing with a step gradient: 200 V (0.01H), 3500V(1.5H), 3500V(2H). Strips were equilibrated in SDS buffer (2% SDS, glycerol, BME, 6M urea) for 15 min at room temperature, separated on 4–12% Bis-Tris gels and blotted to a PVDF membrane.

The approximate isoelectric point (pI) of S. neurona proteins separated by 2D electrophoresis was determined from comparison with carbamylated protein standards. The standards were amylogulcosidase, 89 and 70 kDa, pI 3.8; ovalbumin 45 kDa, pI 5.1; carbonic anhydrase 29 kDa, pI 7.0; myoglobin 17 kDa, pI 7.6. The SnSAG1 reading frame codes for a polypeptide of 276 amino acids and a pI of 7.48. A spot that migrated at an apparent molecular weight of about 29 kDa and a pI of about 7.4 was observed on the blot.

CSF fluid from a horse with EPM was used to probe S. neurona antigens that were separated in two-dimensional gels, blotted to PVDF membranes. The antigens of S. neurona recognized by CSF from a horse diagnosed with EPM were demonstrated. Those antigens identified by equine antisera were compared with those detected when similar blots were probed from a hyperimmunized rabbit.

In an effort to elucidate the difference in antigens recognized by equine CSF and polyclonal rabbit anti-S neurona sera, further experiments were done. Antigens were immunoprecipitated and separated by SDS-PAGE on a 4–12% Bis Tris gradient gel. The most outstanding observation was that a horse with histologically confirmed case of EPM precipitated the 30 kDa antigen that is detected by the rabbit antisera, but does not recognize this as the major antigen on a blot when probed with equine CSF. Likewise, the rabbit antisera precipitated the 19 kDa antigen, but recognized the 30 kDa antigen as the predominant antigen. Although the rabbit antisera does not detect the 19/17 kDa antigen as dominant, when used to probe CSF immunoprecipitated antigens, the rabbit antisera was a better capture reagent than the equine CSF.

The polyclonal rabbit anti-S. neurona antibodies were then used to concentrate the antigen by immunoprecipitation. The same blotted antigens detected with polyclonal rabbit anti-S. neurona antisera. The horse CSF antibodies percipitated antigens that separated at approximately 28 kDa, however, the major antigens recognized by the horse were at 19 kDa. The rabbit recognized major antigens at 29 kDa.

Example 7

Production of Anti-SnSAG-1 Antibodies

A mouse was immunized with S. neurona whole cell antigen and responded with an ELISA titer of greater than 1:8,000 to S. neurona cultured merozoites. Antibodies to whole mouse immunoglobulin molecule serum levels showed a good response to S. neurona but not host cells. The antibodies were determined to be predominantly IgG. No appreciable titer to host cells was observed before or after immunization.

A hybridoma clone termed 1631 that secretes an anti-SnSAG-1 monoclonal antibody was produced by immunizing a mouse with whole *S. neurona* parasites followed by routine fusion with myeloma cells. A well (1631) from the 96 well plate was tested and found to contain a monoclonal antibody (isotype $IgG_1$) to *S. neurona*. The cells were subjected to cloning by limiting dilution and transferred to a 24 well plate and cultured. This culture supernatant of 1631 reacted by ELISA at greater than 1:16,000 and immunoblotted whole cell *S. neurona* antigens to a single band but not to host cells. Analysis of the supernatants from this culture indicated that it contained a monoclonal antibody that specifically bound (a) a 29 kDa band of blotted *S. neurona* antigens, and (b) the surface of whole formalin-fixed or methanol-fixed parasites by IFA and immunogold labeling EM. Epitopes were not removed by periodate treatment as indicated by ELISA and immunogold labeling EM. The 1631 antibody did not react to host cells, Neospora or *T. gondii* by immunoblot. The 1631 antibody was used in an ELISA to determine cross-reactivity with two non-*S. neurona* Apicomplexan parasites known to infect horses. The data indicated that 1631 does not bind *Neospora hughesi* merozoites, *Toxoplasma gondii* tachyzoites, or host cells.

The 1631 antibody preparation reacted with live cells or formalin fixed *S. neurona* but not host cells. Similar results were obtained with methanol fixed parasites. The phase contrast image of the same field demonstrated that there was no binding to host cells. The controls for this experiment, pre-immune mouse serum and isotype control, also showed no binding to *S. neurona* by immunofluorescence assay. Post-embedding immunogold labeling of *S. neurona* cultured merozoites using 1631 antibodies also showed that the surface of the parasite was labeled. Controls included a mouse monoclonal isotype control. The cloned hybridoma 1631 was used to label the surface of *S. neurona* cultured merozoites by post-embedding immunogold labeling.

Example 8

ELISA Protocols

Standard ELISA protocols were adapted for use to detect the presence of *S. neurona* in a sample. Briefly, Nunc Maxisorp plates were prepared by the addition of 50 μl *S. neurona* antigen or host cell antigen diluted to 10 μg/ml in carbonate-bicarbonate buffer and incubate overnight at 4° C. The plates were washed 4 times and blocked in blocking buffer, 1% bovine serum albumin in 1×PBST (1×PBS, 0.05 Tween 20, 1% sodium azide) and incubated for 60 min. at room temperature. One hundred microliters of primary antibody at several dilutions (1631 mAb, mouse pre-immune serum, IgG, 1% BSA without serum, or media) was incubated for 1 hour at room temperature followed by four washes in blocking buffer. A commercial rabbit anti-mouse whole molecule (Sigma A 1902), goat anti-mouse IgG γ chain specific (Sigma A3438), or goat anti-mouse IgM μ chain specific (Sigma A 9688) alkaline phosphatase conjugated secondary antibody was added and incubated for 60 min., washed three times with PBST followed by the addition of para-nitrophenyl phosphate. The OD was measured and recorded at 492 nm at 30 and 60 min to provide results.

Example 9

Probing Clinical Tissues for the Identification of *S. neurona*

Rabbit anti-*S. neurona* antisera and 1631 monoclonal antibodies were used to probe clinical tissues for the identification of *S. neurona*. In one instance, the 1631 antibody was used to detect *S. neurona* in the spinal cord of a horse with clinical signs of EPM. The hyperimmune rabbit antisera also identified merozoites in clinical tissue. Both reagents clearly identified parasites in host tissues that were otherwise identified ambiguously when observed by hemosin and eosin stain.

The 1631 antibody was examined in a competitive ELISA to determine the use of this assay in the measurement of antibodies in clinical samples. The assay used 1631 in a competitive ELISA that measured the percent of inhibition of 1 microgram/ml of 1631 by equine serum and CSF. Although serum did competitively inhibit binding, CSF did not. The media used to prepare monoclonal antibodies was also found to compete for the antibody binding site.

Example 10A

Cloning and Expression of cDNAs Encoding Surface Antigens of *S. neurona*

*S. neurona* merozoites were cultured as previously described. Ellison, S. P. et al., 2000, Vet. Parasitol., 1982:1–11. In this example, merozoites at twelve days post infection were released with calcium ionophore and harvested in Hanks buffered salt solution. Washed merozoites were added to RNAzol as per manufacturer recommendations. The total RNA was separated on a denaturing formamide gel to evaluate the amount of host cell contamination. Vercammen, M. et al., 1998 Parasit. Immnol., 20(1):37–47. The separation of polyadenylated RNA (polyA RNA) from total RNA was achieved by the use of magnetic beads as per manufacturer recommendations.

Two methods were used to construct a cDNA expression library. The method of Froussard was used to produce a cDNA library in the lambda vector Uni Zap XR. Froussard, Nucleic Acids Research, 20: 2900, 1992. First strand synthesis was prepared using a 26 nucleotide primer containing a random hexameter at the 3' end (universal primer -dN6; 5'-GCCGGAGCTCTGCAGAATTCNNNNN-3') (SEQ ID NO:4). *S. neurona* poly A RNA was suspended in 6 ml of distilled water, heated to 65° C. for 5 min, rapidly cooled on ice and reverse transcribed after addition of 0.5 ml (20 U) RNAsin, 1.25 ml 10×reverse transcription buffer (500 mM Tris-HCl, pH 8 at 43° C., 800 mM NaCl, 80 mM $MgCl_2$, 50 mM DTT), 1.25 ml dNTP (10 mM), 1.5 ml universal primer-dN6 (0.1 mg/ml), 2 ml (16 U) AMU reverse transcriptase. Incubation was at 43° C. for 1 hour. The reaction was then boiled for 2 min. and rapidly cooled on ice. For second strand cDNA synthesis the following components were added: 24.25 ml $dH_2O$, 10 ml 5×Klenow buffer, 1.25 ml 5 methyl dCTP (100 mM), and 2 ml Klenow fragment (8 U). After 30 minutes incubation at 37° C., the sample was purified on a chromaspin-400 column (Clontech) to remove the universal primer d-N6 (sample 511). One microliter of the randomly synthesized double stranded cDNA population was amplified in the presence of 1 mM universal primer in a 50 ml reaction mix containing 50 mM KCl, 1.5 mM $MgCl_2$, 0.01% gelatin, 500 mM each dNTP and 1.5 U TAQ polymerase. The samples were subjected to 40 cycles of amplification: 94° C. 1 min., 55° C. 1 min., and 72° C. 3 min. Final amplification products analyzed on a 0.8% agarose gel. The amplified cDNA fragments were ligated to EcoR1 adapters and separated on a drip column containing Sepharose CL-2B gel filtration medium. The size fractionated cDNA was precipitated and ligated to the Uni Zap XR vector. The lambda library was packaged into a high efficiency Gigapack III gold packaging extract and plated on the *E. coli* cell line XL1-Blue MRF-.

A second cDNA expression library was constructed in the lambda vector Uni Zap XR (Stratagene) as per the manufacturer's recommendations. PolyA RNA was converted into double stranded cDNA using the ZAP cDNA synthesis kit and subsequently ligated with Novagen PST Blue perfectly blunt cloning kit (PST Blue-1 vector has EcoR1 sites flanking cloning sites). After in vitro packaging and transfection of host cells (XL1-Blue MRF-) the primary library was amplified to yield a high titer phage stock.

To screen for recombinant phage clones expressing a putative surface antigen of *Sarcocystis neurona* both a monoclonal antibody (antibody from 1631 culture supernatant) and polyclonal rabbit anti-*S. neurona* antibodies were used. The library was also screened with a second monoclonal antibody, 2A7 (a gift of Antoinette Marsh). Analysis of this antibody indicated that it specifically bound (a) the surface of *S. neurona* as determined by by IFA, and (b) a 29 kDa antigen of blotted *S. neurona* parasites. The 2A7 antibody was also subjected to IFA, immunogold labeling electron microscopy, and western blotting for the recombinant work.

Polyclonal anti-*S. neurona* rabbit antibodies were produced by Lampire Laboratories with whole antigen that had been fresh frozen and shipped. Screening was performed according to standard procedures. Primary antibodies were diluted 1:500. Alkaline phosphatase-conjugated goat anti-mouse IgG or goat anti-rabbit IgG were used as secondary antibodies (dilution 1:3000). Positively reacting phage plaques were isolated and subjected to 3 additional rounds of screening. Positive phage clones were converted into pBluescript SK (−) phagemids by means of in vivo subcloning.

The in vivo excision protocol (Stratagene) was followed. Briefly, 1 ml of the amplified library was diluted by addition of SM buffer to give 400 pfu/ml. Overnight cultures of XL1-Blue MRF- and SOLR, supplemented with 0.2% (w/v) maltose and 10 mM $MgSO_4$ were centrifuged and the media removed. The cells were resuspended to an $OD_{600}$ of 1 in 10 mM $MgSO_4$. Two hundred microliters of XL1-Blue MRF- were added to 250 ml ($1\times10^5$) phage and 1 ml Ex Assist helper phage ($1\times10^6$ pfu/ml) and incubated at 37° C. for 15 minutes in a Falcon 2059 polypropylene tube. Three ml LB broth was then added and the tube incubated 2 hours at 37° C. with shaking. The tube was then heated to 70° C. for 20 minutes and centrifuged at 1000×g for 15 min. The supernatant containing the excised pBluescript phagmid was plated by adding 200 ml SOLR cells to 100 ml phage supernatant, and the mixture was incubated for 15 min at 37° C. Two hundred ml of the cell mixture was plated on LB-ampicillin agar plates (50 mg/ml) and incubated overnight.

Additionally, 96 random phagmids were selected, grown overnight, and plasmids isolated by standard mini-prep procedures. The isolated plasmids were sequenced and one candidate clone, C10, was selected based on BLAST analysis. Altschul, S. F. et al., 1997 Nuc. Acids Res., 25:3389–3402. The cDNA library was screened by hybridization with a digoxigenin-labeled probe (EcoR1/Xho1), a fragment from clone CIO. Sequence analysis of one clone revealed a full-length copy of the gene that contained the C10 fragment, a gene with significant similarity to the major surface antigen of *S. muris* (smMSA1).

PCR primers 5' GGGGGGATCCGATGAC-GAGGGCGGGTGCTGCTG (SEQ ID NO:5) and 3' GGGGGATCCTTAGCAAAAGTGCAAGAAAGCG (SEQ ID NO:6) were designed by adding a BamH1 nucleotide sequence to the sequence encoding the 5' and 3' flanking ends of the open reading frame of the full gene encoding the putative surface antigen of S. neurona. A standard 50 ml PCR reaction using 1 ml second strand synthesis reaction as template was used. The single amplification produced by PCR was isolated by electrophoresis and cut out of a low melting agarose gel followed by TOPO (Invitrogen) cloning. One colony was selected. The size of the insert was determined by electrophoresis and the sequence was confirmed by sequence analysis. The DNA was then cloned into the BamH1 site of pBluescript, transfected into XL1-Blue MRF—, and color selected. The DNA from the positive colony was sub-cloned into an expression vector for protein expression. Expression of fusion protein-The cDNA insert from clone 1631-5 and C10-511 was subcloned into the BamH1 site of the expression vector pet14b. This vector allows the expression of the target gene in E. coli under the control of strong bacteriophage T7 promoter. The gene was established in the non-expression host XL1-B. Plasmids were then transferred into the expression host p21 that contains a chromosomal copy of the T7 RNA polymerase gene under lacUV5 control. Expression was induced by the addition of 0.4 mM IPTG. Additionally, this vector contained a HIS "tag" which facilitates detection and purification of the target protein. The gene for ampicillin resistance, (b-lactimase), is contained in the plasmid in the same orientation as the target gene. Forty colonies of bacteria containing the C10–511 gene that grew on ampicillin containing LB plates after overnight incubation were selected and mini-preps prepared. DNA digests using Sma1 and BamH1 were used to select recombinants in the correct orientation. Seven recombinants in the correct orientation were identified. The 1631 recombinants did not allow selection of the correct orientation by DNA digestion. Ten recombinants were selected from ampicillin containing LB plates after overnight incubation. The presence of the 1631 gene was determined by PCR amplification using primers that were developed to add BamH1 sequence to the gene for cloning into p21 and primers used in sequencing the insert. The correct orientation was selected by the size of the resulting PCR product.

The ATG codon at the beginning of the reading frame is preceded by two in-frame termination codons at positions −39 and −66 in the 5' upstream region. The 828 bp reading frame codes for a polypeptide of 276 amino acids with a calculated molecular mass of 28,328 is daltons and an isoelectric point (pI) of 7.48. This sequence appears to encode a membrane protein with a cleavable signal peptide and one transmembrane spanning region near its C terminus. McGeoch 1985 1949/id; Hartmann, Rapoport, et al. 1989 1950/id. It has a potential cleavage site at Ala 255 suggesting a possible GPI anchor at this position. Eisenhaber, Bork, et al. 1999 1951/id. The sequence has 12 cysteine residues, 10 of which are conserved when compared with SmSAG1, and 9 are conserved when the comparison is extended to N. caninum SAG1 (NcSAG1, GenBank No. AF132217). Examination of the genomic DNA encoding SnSAG-1 by PCR indicated that the genomic sequence was slightly larger than that of the cDNA. Sequence analysis indicated the presence of a single 128 bp intron located at position 406/407 in the coding region of the mature mRNA. Overexpression of SnSAG-1 in E. coli using pET14b produced a recombinant protein, with an N-terminal sequence containing 6 His residues, that is slightly larger than the native antigen 29 kDa.

Bacteria carrying the recombinant plasmid for C10–511 were grown to an $A_{600}$ of 0.6 in a 50 ml culture. Twenty ml of culture was added to 1 liter of LB-ampicillin broth (50 mg/ml) and grown to an $A_{600}$ of 0.6. Isopropl thyogalactoside (IPTG) was then added to a final concentration of 0.4 mM and incubation was continued for 2 hours. After harvesting the cells, the fusion protein was detected by immunoblot using anti HIS-tag monoclonal antibody.

Example 10B

Cloning and Expression of cDNAs Encoding Surface Antigens of S. neurona

S. neurona merozoites were cultured as previously described. Ellison, S. P. et al., 2000, Vet. Parasitol., 1982:1–11. In this example, merozoites at twelve days post infection were released with calcium ionophore and harvested in Hanks buffered salt solution. Washed merozoites were added to RNAzol as per manufacturer recommendations. The total RNA was separated on a denaturing formamide gel to evaluate the amount of host cell contamination. Vercammen, M. et al., 1998 Parasit. Immnol., 20(1):37–47. The separation of polyadenylated RNA (polyA RNA) from total RNA was achieved by the use of magnetic beads as per manufacturer recommendations.

A cDNA expression library was constructed in the lambda vector Uni Zap XR (Stratagene) as per the manufacturer's recommendations. An oligo dT primer with a linker containing an XhoI restriction site was used to prime for 1st strand cDNA synthesis using MMLV reverse transcriptase but including 5-methyl dCTP to hemi-methylate the transcripts. This protects the cDNA from later XhoI digestion while leaving the unmethylated linker primer open to digestion. After 1st strand synthesis, 2nd strand synthesis was performed by treating with RNase H and DNA polymerase I. The ends of the double stranded cDNA molecules produced in this reaction were polished using Pfu DNA polymerase, ligated to EcoRI adaptors and phosphorylated. XhoI digestion was performed preparing the transcripts for directional cloning into the Unizap XR vector and size fractionated over a Sepharose CL-2B column. These cDNA inserts were ligated into the Unizap XR cloning vector and the ligation mixture was packaged into functional lambda phage partices using the Gigapack Gold packaging extract (Stratagene, Inc.).

The in vivo excision protocol (Stratagene) was followed to provide excised phagemids from the primary UniZAP library. Ninety-six of these randomly selected phagmids were grown overnight, and plasmids isolated by standard mini-prep procedures. The isolated plasmids were sequenced and the data were analyzed by BLAST comparison against the nr database at NCBI (Altschul, S. F. et al., 1997 Nuc. Acids Res., 25:3389–3402). Two candidate clones, C11 and F03, were identified by sequence similarity with the major surface antigen of S. muris (smMSA1). The cDNA library was screened by hybridization with $^{32}$P-labeled insert from the C11 clone yielding a large number of phage clones hybridizing with this probe. Six of these positive clones were selected and sequenced yielding the complete sequence of the coding region. PCR primers JNB 162-(ACGAGGATCCGATGACGAGGGCGGTGCTG CTG) (SEQ ID NO:7) and JNB 163-(ACGAGG ATCCCACGGCAGGATTAGCAAAAGTGC) (SEQ ID NO:8) were designed to add a BamH1 recognition sequence for cloning into the pET14b expression vector (Novagen). The pool of cDNA prepared from merozoite mRNA was used as template. The single amplification produced by PCR was isolated by electrophoresis and cut out of a low melting agarose gel followed by TOPO (Invitrogen) cloning. One colony was selected. The size of the insert was determined by electrophoresis and the sequence was confirmed by sequence analysis. The DNA from the positive colony was sub-cloned into pET14b for protein expression. The insert was released by BamHI digestion, purified by low melting agarose gel electrophoresis and ligated into the pET14b vector. Orientation was determined by restriction digestion with SmaI. Seven recombinants in the correct orientation were identified.

In the largest cDNA clone the ATG codon at the beginning of the reading frame is preceded by two in-frame termination codons at positions −39 and −66 in the 5' upstream region. The 828 bp reading frame codes for a polypeptide of 276 amino acids with a calculated molecular mass of 28,328 daltons and an isoelectric point (pI) of 7.48. This sequence appears to encode a membrane protein with a cleavable signal peptide and one transmembrane spanning region near its C terminus. McGeoch 1985 1949/id; Hartmann, Rapoport, et al. 1989 1950/id. It has a potential cleavage site at Ala 255 suggesting a possible GPI anchor at this position. Eisenhaber, Bork, et al. 1999 1951/id. The sequence has 12 cysteine residues, 10 of which are conserved when compared with SmSAG1, and 9 are conserved when the comparison is extended to N. caninum SAG1 (NcSAG1, GenBank No. AF132217). Examination of the genomic DNA encoding SnSAG-1 by PCR indicated that the genomic sequence was slightly larger than that of the cDNA. Sequence analysis indicated the presence of a single 128 bp intron located at position 406/407 in the coding region of the mature mRNA. Over-expression of SnSAG-1 in E. coli using pET14b produced a recombinant protein, with an N-terminal sequence containing 6 His residues, that is slightly larger than the native antigen 29 kDa.

Bacteria carrying the recombinant plasmid for C10-511 were grown to an $A_{600}$ of 0.6 in a 50 ml culture. Twenty ml of culture was added to 1 liter of LB-ampicillin broth (50 mg/ml) and grown to an $A_{600}$ of 0.6. Isopropl thyogalactoside (IPTG) was then added to a final concentration of 0.4 mM and incubation was continued for 2 hours. After harvesting the cells, the fusion protein was detected by immunoblot using anti HIS-tag monoclonal antibody.

Example 11

Southern and Northern Blot Hybridization

S. neurona merozoites were harvested from 12 days post-infection cultures and the total DNA was extracted using standard procedures. Briefly, the whole cells were pelleted in PBS. The pellet was suspended in lysis buffer (1M Tris, pH 8, 0.5M EDTA, pH 8, 5 M LiC1, Triton X 100). An equal volume of phenol: chloroform: isoamyl alcohol (1:1:25) was added and mixed by inversion for 2 minutes. The suspension was centrifuged at 10,000 rpm in a microfuge at 4° C. for five minutes to separate the liquid phases. The aqueous phase was removed to a new tube and two and one half volumes 100% EtOH was added and incubated for 20 min at −20° C. The precipitated DNA was pelleted by centrifugation at 14,000 rpm for 20 min at 4° C. The pellet was washed in 80% EtOH, air dried and resuspended in 50 ml TE. DNA extracted from T. gondii and Neospora served as controls. DNA (5 mg) aliquots were digested with EcoR1 or BamH1 and electrophoresed on a 0.8% (w/v) agarose gel. Southern blotting was preformed by capillary transfer onto nylon membranes following acid depurination, alkaline denaturing, and neutralization steps.

Hybridization probes were generated by PCR isolated recombinants. The primers: 5' GGGGGGATCCGATGAC-GAGGGCGGGTGCTGCTG (SEQ ID NO:5) and 3' GGGGGATCCTTAGCAAAAGTGCAAGAAAGCG (SEQ ID NO:6) (in other experiments primers JNB 162 and JNB 163 were used) were used in a standard PCR reaction with one microliter of DNA from a clone that contained the open reading frame of the gene SnSAG-1. The resulting single PCR band was diluted and an aliquot labeled with $^{32}P$ by random priming. This probe was used in hybridization to DNA and mRNA from whole S. neurona, T. gondii, Neospora, and S. falcatula. The blots were hybridized using 1×SSC at 60° C. Bands were visualized using manufacturer recommendations.

For Northern analysis, RNA was produced as described above and was analyzed by agarose/formaldehyde gel electrophoresis. The RNA, 1 μg, was transferred to a nylon membrane. After pre-hybridization (2×SSC containing salmon sperm DNA) for two hours at 60° C., a probe prepared from the open reading frame of SnSAG-1 was $^{32}P$ labeled by the random primer method and added to the hybridization buffer for 24 hours at 60° C. Feinberg, A. P. and Vogelstein, B., 1984 Anal. Biochem., 137:266–267. The membrane was washed in 0.2×SSC, 0.2% SDS at 55° C. Autoradiography was performed with enhancing screens for 8 days at −80° C. The probe was also used to hybridize blots of DNA from S. neurona, T. gondii, N. caninum, and S. falcatula. Bands were visualized by autoradiography.

Clones from a cDNA library constructed from the mRNA of S. neurona merozoites cultured in vitro were randomly sequenced. Partial sequence of one clone containing a 687 bp insert when translated into an amino acid sequence had 32% identity to the major surface antigen of S. muris (SmMSA1). This partial clone was used as a probe to obtain a full-length copy of the coding region of the gene. Screening the library by hybridization with this probe demonstrated that ~10% of clones screened bound this probe. Analysis of seven positive clones revealed that many of the cDNA inserts were partial clones of similar length (~0.83 kb), and they shared a common restriction map (data not shown). One larger clone had an extended 5'-untranslated region with a total insert size of 1232 base pairs. The sequence of this longer clone contains a 5' noncoding region of 72 bp, a single long open reading frame of 828 bp, and a 333 bp 3' nontranslated region. When the probe was hybridized to a blot of total RNA isolated from S. neurona, one extremely strong band was detected at 1.5 k. It thus appears that the cDNA clone sequenced contains most of the major mRNA transcript. This probe also hybridized to S. neurona DNA fragments but not to bovine host cell DNA. A blot of EcoR1-cleaved DNA hybridized with this probe yields a single band at approximately 1.2 kb.

Example 12

Preparation of rSnSAG-1

Four liters of induced cells were collected by centrifugation at 6000 rpm in a JB6 rotor 1000×g at 4° C. for twenty minutes. Cells were resuspended in 25 ml TN buffer (50 mM Tris, pH 7.4, 150 mM NaCl). Several methods were compared including freeze/thaw and sonication for the release of inclusion bodies. A higher yield of recombinant protein was released when a French press was used to rupture the cells. The cells were disrupted by passing through a French press twice at 2200 PSI. One-fourth of the mixture was then layered over a 28 ml 27% sucrose cushion and centrifuged at 9000 rpm for 30 min at 10° C. using a SW41 rotor at 7000×g in an ultracentrifuge. This step was repeated.

The resulting pellet was resuspended in one ml TN buffer, divided into 250 ml aliquots in microfuge tubes and stored at −20° C. One aliquot was mixed with 6M urea in 1×bind buffer (40 mM imidazole, 4M NaCl, 160 mM Tris, pH 7.9) and stirred for 40 minutes at 4° C. The solution was centrifuged at 9000 rpm for 30 minutes at 5° C. A His-Tag column was prepared by washing 2 ml resin with three volumes distilled water followed by six volumes 8×charge buffer (400 mM NiSO4) diluted to 1× with distilled water. The column was washed with three volumes 1×binding buffer containing 6M urea. The sample was added and the column washed with 10 volumes 1×bind buffer containing 6M urea, 6 volumes 1×wash buffer made by diluting 8× wash buffer (480 mM imidazole, 4 M NaCl, 160 mMTris pH 7.9) with distilled water. The sample was eluted using 1×strip buffer diluted from a 4×stock (400 mM EDTA, 2 M NaCl, 80 mM Tris pH 7.9). The sample was then dialyzed to remove urea and salts using 20 mM Tris pH 8 with 1% Triton X. The buffer was changed three times over 24 hours.

Over-expression of SnMSA-1 in *E. coli* using pET 14b produced a recombinant protein of 29 kDa, pI 7.3, with an N-terminal extension containing 6 His residues and a thrombin cleavage site. Purification of the recombinant protein was achieved using a His-tag column. The His-tag was confirmed by N-terminal sequencing and was recognized on immunoblots by His-tag monoclonal antibody. Carbamylated protein standards were used to determine the pI of rSnMSA-1 focused on IPG strips at pI 7.3. Thrombin cleavage of the recombinant protein to release the His-tag yielded rSnMSA-1 that was recognized on immunoblots by mAbs 1631, 2A7, polyclonal monospecific mouse anti-rSnMSA1, equine serum and CSF, but not serum from European horses or monoclonal isotype controls. Cleavage of the His-tag from the recombinant protein decreased the apparent molecular weight slightly as detected by SDS-PAGE analysis. Monospecific anti-rSnMSA-1antisera bound native *S. neurona* surface antigens by IFA, post embedding immunogold labeling and ELISA confirming the identity of this clone as a surface antigen of this parasite.

Example 13

Capture ELISA was used to Quantitate *S. neurona* Antigens

Antibodies raised against *S. neurona* were used to quantitate rSnSAG-1 that bound in a capture ELISA. The capture ELISA using rSnSAG-1 served as a standard to measure the amount of SnMSA-1 used in preparative samples for immunoblot. First, recombinant protein was used in an ELISA to titer purified IgG from polyclonal rabbit anti-*S. neurona* antibodies. A second aliquot of purified antibody was biotinylated and used as a reagent to detect antigen captured by antibodies, this reagent was also quantitated using against rSnSAG-1. Both protein G purified and biotinylated protein G purified rabbit anti-*S. neurona* were used to configure a capture ELISA. 96 well plates were coated with protein G purified rabbit anti-*S. neurons*, followed by the addition of diluted rSnSAG-1. After incubation and washing using standard conditions biotinylated protein G purified rabbit anti-*S. neurona* was added, incubated, and washed. The detection of the biotinylated antibodies was accomplished with the addition of alkaline phosphatase-Strepavadin (P-NPP,(Sigma N2765) and the absorbance read at 405 nm. Additionally, the purified rabbit anti-*S. neurona* was used as the capture antibody and monoclonal antibodies directed against SnMSA-1 were used for detection of protein captured. Monospecific anti-rSnMSA-1 antisera bound native *S. neurona* surface antigens by ELISA confirming the identity of this clone as a surface antigen of this parasite.

Example 14

Localization of SnSAG-1 on Surface of *S. neurona* Merozoites

Standard IFA protocols were used, but fixation of the parasites varied. *S. neurona* was grown in BM cells on glass slides that were coated with collagen followed by fixation in methanol or formalin. Parasites were harvested from 150 cm$^2$ flasks and washed with PBS and used fresh or prepared by cytospin and fixed with methanol or formalin. Slides were blocked with the application of 100 µl dilute goat serum for 30 min. at 37° C. to block non-specific binding. Slides were washed in PBST bath for 5 min. with three changes of buffer, drained of excess fluid and primary antibody.

Monoclonal antibodies 1631 and 2A7 bound strongly to *S. neurona* merozoites as viewed by immunofluorescence microscopy. Parasites were examined by transmission electron microscopy after immunogold labeling using standard procedures used at the ICBR Electron Microscopy Core at the University of Florida. Briefly, parasites were embedded in epoxy for transmission electronmicroscopy. Grids containing thin sections were incubated with mAb control sera, mAb 2A7, or mAb 1631 and incubated for one hour at room temperature. Secondary anti-mouse antibodies conjugated to 15 nm gold beads were applied. Stained sections were subsequently viewed by transmission electron microscopy. Gold-labeled, anti-mouse antibodies bound the surface of the embedded parasites treated with either mAb 2A7 or mAb 1631.

Example 15

Immunoblot Analysis

Monoclonal antibodies 1631 and 2A7 bound a 29 kDa antigen on immunoblots of SDS-PAGE separated native antigens derived from cultured *S. neurona* merozoites. The immunodominance of antigen(s) at ~29–30 kDa in a mouse immunized with merozoites suspended in adjuvant was evident. Binding of mAb2A7 and mAb1631 to an antigen at 29 kDa was evident. When the antigen preparation is reduced by heating in the presence of β-mercaptoethanol, binding of both monoclonal antibodies was greatly reduced or abolished. Neither of these monoclonal antibodies bound to host cell antigens nor to *N. caninum* or *T. gondii* tachyzoite antigens on immunoblots.

The rSnSAG-1 was recognized on immunoblots by His-tag monoclonal antibody, mAb 2A7, CSF from a horse with clinical EPM, but not by serum from European horses never exposed to *S. neurona*. Monoclonal antibodies 2A7 and 1631 bind to epitopes on rSnSAG-1 that are sensitive to reduction with sulfhydryl reducing agents, but amounts of β-mercaptoethanol twice normal are necessary to eliminate the epitope from rSnSAG-1 on western blots. IgG1 control antibody does not bind to rSnSAG-1 non-reduced or reduced. Serum from a horse with clinical EPM binds to rSnSAG-1 in a fashion similar to the mAbs 2A7 and 1631. When β-mercaptoethanol is increased in the sample buffer from 5 to 10%, the amount of detectable rSnSAG-1 is greatly reduced.

Results of the above experiments determined that both monoclonal antibody 2A7 and the rabbit polyclonal antibody bound the recombinant protein as well as a 29 kDa protein of the cultured parasite. The recombinant protein was detected as a 30 kDa band when the His-tag remained on the protein. In parallel experiments, equine CSF from a histopathologically confirmed case of EPM, but not European equine sera, was also shown to bind the 29 kDa band.

Protein samples including merozoites and rSnSAG-1 were suspended in 4×sodium dodecyl sulfate polyacryamide gel electrophoresis (SDS-PAGE) loading buffer without reducing agents (1.09 M glycerol, 141 mM Tris base, 106 mM Tris HCL, 73 mM lithium dodecyl sulfate, 0.51 mM EDTA, 0.22 mM Serva Blue G250, 0.175 mM phenol red, pH 8.5). After boiling, samples were loaded onto 4–12%

New Page Bis Tris gels. For Western blot analysis, proteins were transferred onto PVDF membranes and immunodetection as described below. Briefly, 10 mg of purified parasites or protein preparations were electrophoresed on 4-Bis-Tris 12% reducing or non-reducing gels and transferred to PVDF membranes. PVDF membranes were blocked for one hour in PBS with 5% non-fat dry milk and 2% Tween 20.

Rabbit anti-S. neurona polyclonal (polyclonal antibodies were made by immunizing a rabbit with an antigen prearation made from the UCD 1 isolate) or specific monoclonal antibody (2A7, a gift of Antoinette Marsh) was used as a primary antibody. Primary antibody was diluted in blocking buffer at 1:500 was incubated on a rotary shaker for two hours at room temperature. Membranes were washed for one hour with three changes of blocking buffer. Alkaline phosphatase-conjugated secondary antibody was diluted to manufacturer's recommendations (1:15,000) and incubated at room temperature on a rotary shaker for one hours. Membranes were washed for one half hour with three changes of blocking buffer. Chromogenic detection of antibody was preformed as the manufacturer recommended (Invitrogen Westernbreeze chromogenic kit # WB7103 and WB7105). Pooled sera from 6 European horses that were never exposed to *S. neurona* was used as a negative control. Serum and cerebral spinal fluid from an *S. neurona*-infected equine were obtained from the horse from which the UCD 1 isolate was cultured. Marsh, A. E. et al., JAVMA, 209(11) 1907–1913.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A composition for stimulating an immune response against *Sarcocystis neurona* when administered to an animal, the composition comprising:
   (a) an isolated polypeptide comprising the amine acid sequence as set forth in SEQ ID NO:1; and
   (b) a pharmaceutically acceptable carrier.

2. The composition of claim 1, wherein the composition comprises an adjuvant.

3. The composition of claim 2, wherein the adjuvant comprises a substance selected from the group consisting of: an aluminum salt; an oil-in-water emulsion; a composition comprising saponin; a composition comprising a bacterial protein; and a cytokine.

4. A composition for detecting the presence of *S. neurona* in a biological sample comprising an isolated polypeptide as set forth in SEQ ID NO:1.

5. The composition according to claim 4, wherein the polypeptide is fused, in frame, to another polypeptide.

6. The composition according to claim 4, wherein the polypeptide is a recombinant protein.

7. An isolated polypeptide comprising the amino acid sequence as set forth in SEQ ID NO:1.

8. The isolated polypeptide of claim 7, wherein the polypeptide is fused, in frame, to another polypeptide.

9. The isolated polypeptide of claim 7, wherein the polypeptide is a recombinant protein.

10. The composition according to claim 4, further comprising a pharmaceutically acceptable carrier.

11. The composition according to claim 1, wherein said polypeptide is fused, in frame, to another polypeptide.

* * * * *

UNITED STATES PATENT AND TRADEMARK OFFICE
CERTIFICATE OF CORRECTION

PATENT NO. : 6,808,714 B2
DATED : October 26, 2004
INVENTOR(S) : John B. Dame, Siobhan P. Ellison and Charles A. Yowell, Jr.

It is certified that error appears in the above-identified patent and that said Letters Patent is hereby corrected as shown below:

Column 2,
Lines 15-16, "used to gusto prepare" should read -- used to prepare --

Column 8,
Line 56, "93%, 97%" should read -- 93%, 94%, 95%, 96%, 97% --
Line 62, "62%, 66%" should read -- 62%, 63%, 64%, 65%, 66% --
Line 63, "78%, 82%" should read -- 78%, 79%, 80%, 81%, 82% --
Line 65, "94%, 98%" should read -- 94, 95%, 96%, 97%, 98% --

Column 9,
Line 9, "67%, 71%" should read -- 67%, 68%, 69%, 70%, 71% --
Line 9, "83%, 87%" should read -- 83%, 84%, 85%, 86%, 87% --

Column 26,
Line 59, "CI0" should read -- C10 --

Column 27,
Line 45, "28,328 is daltons" should read -- 28,328 daltons --

Column 31,
Line 50, "neurons" should read -- neurona --

Signed and Sealed this

Thirty-first Day of May, 2005

JON W. DUDAS
*Director of the United States Patent and Trademark Office*

UNITED STATES PATENT AND TRADEMARK OFFICE
CERTIFICATE OF CORRECTION

PATENT NO.   : 6,808,714 B2
DATED        : October 26, 2004
INVENTOR(S)  : John B. Dame, Siobhan P. Ellison and Charles A. Yowell, Jr.

It is certified that error appears in the above-identified patent and that said Letters Patent is hereby corrected as shown below:

Column 2,
Lines 15-16, "used to gusto prepare" should read -- used to prepare --

Column 8,
Line 56, "93%, 97%" should read -- 93%, 94%, 95%, 96%, 97% --
Line 62, "62%, 66%" should read -- 62%, 63%, 64%, 65%, 66% --
Line 63, "78%, 82%" should read -- 78%, 79%, 80%, 81%, 82% --
Line 65, "94%, 98%" should read -- 94%, 95%, 96%, 97%, 98% --

Column 9,
Line 9, "67%, 71%" should read -- 67%, 68%, 69%, 70%, 71% --
Line 9, "83%, 87%" should read -- 83%, 84%, 85%, 86%, 87% --

Column 26,
Line 59, "CI0" should read -- C10 --

Column 27,
Line 45, "28,328 is daltons" should read -- 28,328 daltons --

Column 31,
Line 50, "neurons" should read -- neurona --

This certificate supersedes Certificate of Correction issued May 31, 2005

Signed and Sealed this

Second Day of August, 2005

JON W. DUDAS
*Director of the United States Patent and Trademark Office*

```
                              SEQUENCE LISTING

<160> NUMBER OF SEQ ID NOS: 8

<210> SEQ ID NO 1
<211> LENGTH: 276
<212> TYPE: PRT
<213> ORGANISM: Sarcocystis neurona

<400> SEQUENCE: 1

Met Thr Arg Ala Val Leu Leu Thr Phe Leu Thr Leu Cys Ser Ala Arg
1               5                   10                  15

Val Ser Leu Val Arg Ala Gly Ala Pro Pro Gln Ala Thr Cys Ala Asn
            20                  25                  30

Gly Glu Thr Thr Val Thr Lys Leu Gly Ser Ser Gly Ala Leu Arg Ile
        35                  40                  45

His Cys Pro Asn Asn Phe Arg Leu Ala Pro Arg Ala Gly Asn Asp Ala
    50                  55                  60

Gly Gln Met Gln Val Tyr Ala Thr Ala Val Ala Glu Asn Pro Val Asn
65                  70                  75                  80

Ile Arg Asp Val Leu Pro Gly Ala Ser Tyr Leu Ser Val Gln Asn Val
                85                  90                  95

Pro Thr Leu Thr Val Pro Gln Leu Pro Ala Lys Ala Thr Ser Val Phe
            100                 105                 110

Phe His Cys Gln Gln Gln Pro Asp Asn Gln Cys Phe Ile Gln Val Glu
        115                 120                 125

Val Ala Pro Ala Pro Arg Leu Gly Pro Asn Thr Cys Ala Ala Leu Gln
    130                 135                 140

Ser Thr Ile Ala Phe Glu Val Gln Gln Ala Asn Glu Thr Ala Val Phe
145                 150                 155                 160

Ser Cys Gly Glu Gly Leu Ala Val Phe Pro Gln Gly Ser Lys Ala Leu
                165                 170                 175

Asp Glu Ala Cys Ser Lys Glu Gln Ala Leu Pro Ser Gly Ala Ala Leu
            180                 185                 190

Ala Pro Lys Asp Gly Gly Leu His Leu Gly Phe Pro Gln Leu Pro Gln
        195                 200                 205

Gln Ala Met Lys Ile Cys Tyr Ile Cys Thr Asn Gly Gly Val Gln Ala
    210                 215                 220

Glu Ala Ala Gln Arg Cys Glu Val Arg Ile Ser Val Ala Ala Asn Pro
225                 230                 235                 240
```

Asp Ser Gly Val Pro Gly Ala Asn Gly Ala Ala Ser Leu Gly Ala Ala
            245                 250                 255

Ala Arg Ser Ala Ser Ala Leu Gly Leu Ala Leu Val Ala Gly Ala Phe
        260                 265                 270

Leu His Phe Cys
        275

<210> SEQ ID NO 2
<211> LENGTH: 1132
<212> TYPE: DNA
<213> ORGANISM: Sarcocystis neurona

<400> SEQUENCE: 2

| | | | | | |
|---|---|---|---|---|---|
| gggaggtaag | tgttggcggt | aatgctgcat | cattagggtc | agacacgctg | tccatctgtc | 60 |
| attctcgcca | gaatgacgag | ggcggtgctg | ctgacgtttc | tgacactctg | ctccgccaga | 120 |
| gtgtcccttg | tgagggccgg | agcgccgcct | caagcacgtg | cgccaatggc | gaaacgactg | 180 |
| ttactaagct | cggcagctct | ggcgcactac | gaatccactg | cccaaataat | tttcgactcg | 240 |
| cgccccgggc | tgggaatgac | gccggtcaga | tgcaggtcta | tgcactgcgg | ttgctgagaa | 300 |
| tcctgtaaac | atacgagacg | tcctgcccgg | cgcatcttac | ctctctgtac | agaacgtccc | 360 |
| gagggtcacc | gtcccgcaat | tgcccgccaa | agctacgagc | gtcttttttc | actgccagca | 420 |
| gcaacccgac | aaccaatgct | tcatccagtc | agctgcggcg | agggacttgc | tgtgttcccg | 480 |
| caaggtagca | aagcgttgga | tgaagcctgc | tccaaagagc | aggccctacc | cagtggcgcc | 540 |
| gctttagctc | caaaggatgg | tgggctccac | cttggttttc | ctcagcttcc | tcagcaggct | 600 |
| atgaagattt | gctatatttg | tacgaatggt | ggtgtgcagg | cagaggcggc | ccaacggtgt | 660 |
| gaggttcgca | tctccgtcgc | agcgaaccca | gacggaagcg | ttccaggggc | taacggagcc | 720 |
| gcctctctag | gagctgccgc | acgcagcgcc | tctgcgttag | ggttggctct | cgttgcaggc | 780 |
| gctttcttgc | acttttgcta | atcctgccgt | gtagcgtctc | tggtggcccg | ccccacagat | 840 |
| cctggttatt | cccacagcgt | gtagcgtctc | tggtggcccg | ccccacagat | cctggttacg | 900 |
| cgttcagtaa | cgtgcctact | gttccaaaac | gggaaaatcc | gaagatgcaa | aattcatccg | 960 |
| gtgcagcgtc | ccatgtgttc | agttacgact | ggacagtgt | agtgagatgg | ttttacatcc | 1020 |
| attcgcagtg | cagaggcgtg | ggctcgcata | tttttttttt | gtagtgtgcc | gttgtagatc | 1080 |
| cagcaagtta | aatatgttag | tcattttgag | cgcctgttcc | acgtaggcgg | ct | 1132 |

<210> SEQ ID NO 3
<211> LENGTH: 729
<212> TYPE: DNA
<213> ORGANISM: Sarcocystis neurona

<400> SEQUENCE: 3

| | | | | | |
|---|---|---|---|---|---|
| atgacgaggg | cggtgctgct | gacgtttctg | acactctgct | ccgccagagt | gtcccttgtg | 60 |
| agggccggag | cgccgcctca | agcacgtgcg | ccaatggcga | aacgactgtt | actaagctcg | 120 |
| gcagctctgg | cgcactacga | atccactgcc | caaataattt | cgactcgcg | ccccgggctg | 180 |
| ggaatgacgc | cggtcagatg | caggtctatg | cactgcggtt | gctgagaatc | ctgtaaacat | 240 |
| acgagacgtc | ctgcccggcg | catcttacct | ctctgtacag | aacgtcccga | gggtcaccgt | 300 |
| cccgcaattg | cccgccaaag | ctacgagcgt | cttttttcac | tgccagcagc | aacccgacaa | 360 |
| ccaatgcttc | atccagtcag | ctgcggcgag | ggacttgctg | tgttcccgca | aggtagcaaa | 420 |
| gcgttggatg | aagcctgctc | caaagagcag | gccctaccca | gtggcgccgc | tttagctcca | 480 |

-continued

```
aaggatggtg ggctccacct tggttttcct cagcttcctc agcaggctat gaagatttgc      540
tatatttgta cgaatggtgg tgtgcaggca gaggcggccc aacggtgtga ggttcgcatc      600
tccgtcgcag cgaacccaga cggaagcgtt ccagggcta acggagccgc ctctctagga       660
gctgccgcac gcagcgcctc tgcgttaggg ttggctctcg ttgcaggcgc tttcttgcac      720
ttttgctaa                                                              729

<210> SEQ ID NO 4
<211> LENGTH: 25
<212> TYPE: DNA
<213> ORGANISM: Artificial sequence
<220> FEATURE:
<223> OTHER INFORMATION: universal primer
<221> NAME/KEY: misc_feature
<222> LOCATION: (21)..(25)
<223> OTHER INFORMATION: n

<400> SEQUENCE: 4
gccggagctc tgcagaattc nnnnn                                            25

<210> SEQ ID NO 5
<211> LENGTH: 33
<212> TYPE: DNA
<213> ORGANISM: Sarcocystis neurona

<400> SEQUENCE: 5 gggggatcc gatgacgagg gcgggtgctg ctg                                    33

<210> SEQ ID NO 6
<211> LENGTH: 31
<212> TYPE: DNA
<213> ORGANISM: Sarcocystis neurona

<400> SEQUENCE: 6 ggggatcct tagcaaaagt gcaagaaagc g                                      31

<210> SEQ ID NO 7
<211> LENGTH: 32
<212> TYPE: DNA
<213> ORGANISM: Sarcocystis neurona

<400> SEQUENCE: 7
acgaggatcc gatgacgagg gcggtgctgc tg                                    32

<210> SEQ ID NO 8
<211> LENGTH: 33
<212> TYPE: DNA
<213> ORGANISM: Sarcocystis neurona

<400> SEQUENCE: 8
acgaggatcc cacggcagga ttagcaaaag tgc                                   33
```